(12) United States Patent
Malek et al.

(10) Patent No.: US 7,585,808 B2
(45) Date of Patent: Sep. 8, 2009

(54) METHODS FOR PREPARING CATALYSTS

(75) Inventors: Andrzel Malek, Baton Rouge, LA (US); James Clarke Vartuli, Schwenksville, PA (US); Stuart Leon Soled, Pittstown, NJ (US); Sabato Miseo, Pittstown, NJ (US); Jennifer Schaefer Feeley, Lebanon, NJ (US); Gary L. Casty, League City, TX (US); Gabor Kiss, Hampton, NJ (US); Jeffrey M. Dysard, Michigan City, IN (US); Joseph Ernest Baumgartner, Califon, NJ (US); Christine E. Kliewer, Clinton, NJ (US); Steven T Ragomo, Perkasie, PA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 412 days.

(21) Appl. No.: 10/534,072

(22) PCT Filed: Nov. 18, 2003

(86) PCT No.: PCT/EP03/12884

§ 371 (c)(1),
(2), (4) Date: Feb. 17, 2006

(87) PCT Pub. No.: WO2004/045767

PCT Pub. Date: Jun. 3, 2004

(65) Prior Publication Data

US 2006/0166809 A1    Jul. 27, 2006

(30) Foreign Application Priority Data

Nov. 20, 2002  (GB) .................. 0227081.7

(51) Int. Cl.
*B01J 23/00*         (2006.01)
(52) U.S. Cl. .................. 502/300; 502/20; 502/240; 502/258; 502/407; 502/415
(58) Field of Classification Search .................. 502/20
See application file for complete search history.

(56) References Cited

U.S. PATENT DOCUMENTS

| 2,650,906 | A | * | 9/1953 | Engel et. al. ................. 502/315 |
| 5,332,705 | A | * | 7/1994 | Huang et al. .................. 502/53 |
| 5,344,553 | A | * | 9/1994 | Shih ............................ 208/49 |
| 5,863,856 | A | * | 1/1999 | Mauldin ....................... 502/325 |

* cited by examiner

*Primary Examiner*—Melvin C Mayes
*Assistant Examiner*—Michael Forrest
(74) *Attorney, Agent, or Firm*—Mel Den; Mandi Milbank

(57) ABSTRACT

The present invention is directed to processes for preparing supported metal catalysts comprising one or more catalytically active metals applied to a porous catalyst support and to processes that use such catalysts. The process requires the formation of an organic complex during the manufacture of the catalyst which after its formation is either partially or fully decomposed before reduction if the metal to form the catalyst. The catalysts have high levels of metal dispersion and uniform distribution of catalytically active metals on the support. The catalysts obtained form the processes are particularly effective in catalysing Fischer-Tropsch reactions and as adsorbants for the removal or organosulfur compounds from hydrocarbons.

37 Claims, 11 Drawing Sheets

METHODS FOR PREPARING CATALYSTS

This application is the National Stage of International Application No. PCT/EP03/12884, filed Nov. 18, 2003, which claims the benefit of Great Britain Application 0227081.7, filed Nov. 20, 2002, the entire disclosures of which are hereby incorporated herein by reference.

FIELD OF INVENTION

The present invention relates to methods for the manufacture of supported catalysts and in particular to methods for the manufacture of supported catalysts comprising one or more active metals deposited on a support.

BACKGROUND OF THE INVENTION

Supported catalysts, in particular supported metal or metal oxide catalysts, are well known in the art. Dispersions of small metal particles on metal oxide substrates are commonly used as catalytic materials. The physical and chemical properties of the final catalyst can depend strongly on the preparation of the substrate prior to deposition of the metal particles, on the methods of deposition used and on any subsequent treatments of the metal/oxide system.

The ability to prepare high loaded metal catalysts that have small particle sizes (high dispersion) and metal particles that are homogeneously distributed on the support surface is an important requirement for effective supported catalysts. In many instances, particularly with base metal catalysts, highly loaded metal catalysts have large metal particles (>10 nm) that are clustered in localized areas on the support. Since catalytic activity of many reactions correlates with the number of available surface metal sites, it is important to be able to produce catalysts with good metal dispersion. Uniformity of the distribution of catalytic metal sites is also an important factor and maximization of the inter-particle distance can help to provide for stable supported catalysts with reduced sintering problems. Supported metal catalysts are often prepared by incipient wetness impregnation of solutions containing metal salts, dried and then calcined to form the oxides. The oxides are then reduced to form the supported metal catalysts.

There have been various attempts in the art to improve the dispersion of active metals deposited on refractory inorganic oxide supports to produce catalysts for use in Fischer-Tropsch processes. In particular there have been various approaches adopted in the art to reduce the amount or rhenium or other group 8 metals required in combination with the catalytic metal.

In published International Patent Application No. WO 98/47618, multifunctional carboxylic acids having from about 3 to 6 total carbon atoms are co-deposited with sources of catalytically active metal onto a refractory metal oxide followed by calcination to prepare Fischer-Tropsch catalysts. Examples of the multifunctional carboxylic acids include various amino acids.

In published International Patent Application No. WO 98/47620, carbohydrate or sugars are either co-deposited with sources of catalytically active metal or are applied after deposition of the source of catalytically active metal onto a refractory metal oxide followed by calcination to prepare Fischer-Tropsch catalysts.

In published International Patent Application No. WO 98/47617, polyols are co-deposited with sources of catalytically active metal onto a refractory metal oxide followed by calcination to prepare Fischer-Tropsch catalysts.

There is a continuing need for new methods for the preparation of supported metal catalysts, which enable the dispersion of metal in the final catalyst to be controlled.

It is therefore an object of the present invention to provide processes for the manufacture of supported metal catalysts, which enables the control of metal dispersion in the catalyst.

SUMMARY OF THE INVENTION

In the processes of the present invention it has been found that by exercising specific control over the reagents and the preparative steps used in the preparation of supported metal catalysts, supported metal catalysts with improved metal dispersion properties may be obtained.

Thus in a first aspect the present invention provides a process for the manufacture of a catalyst which process comprises;
 a) preparing a support having one or more organic complexes of one or more catalytically active metals deposited thereon;
 b) partially decomposing the one or more organic metal complexes deposited thereon; and
 c) converting the one or more partially decomposed organic metal complexes to catalytically active metal.

In a second aspect the present invention provides a process for the manufacture of a catalyst which process comprises;
 a) treating a support with a compound, or salt, of one or more catalytically active metals to provide a support with one or more catalytic metal precursors deposited thereon,
 b) treating the support with one or more catalytic metal precursors deposited thereon with one or more organic compounds to form one or more organic complexes,
 c) partially decomposing the one or more organic complexes; and
 d) converting the one or more partially decomposed organic metal complexes to catalytically active metal.

In a further embodiment of the second aspect prior to treatment of the support with one or more catalytic metal precursors deposited thereon with one or more organic compounds, the support with one or more catalytic metal precursors deposited thereon may be thermally treated by calcination or pyrolysis. In a further embodiment of this aspect steps a) and b) may be reversed; the support may be treated in a first step with one or more organic compounds and the support with one or more organic compounds deposited thereon may be treated with a compound, or salt, of one or more catalytically active metals to form one or more organic complexes on the support, followed by partial decomposition of the one or more organic complexes and conversion to catalytically active metal. In all embodiments of the second aspect the conversion to catalytically active metal may be carried out under reducing conditions e.g. in the presence of a source of hydrogen or CO. The organic compounds are preferably nitrogen containing organic compounds. In the second aspect of the present invention either the treatment with one or more organic compounds or the treatment with one or more compounds, or salts, of one or more catalytically active metals may be omitted if either of these compounds is introduced to the support during its preparation or synthesis.

In a third aspect the invention provides a process for the manufacture of a catalyst which comprises;
 a) treating a porous support with a compound, or salt, of one or more catalytically active metals to provide a porous support with one or more catalytic metal precursors deposited thereon, b) treating the support with one or more catalytic precursors deposited thereon with one or more organic compounds to form one or more organic complexes,
c) fully decomposing the one or more organic complexes deposited thereon; and
d) converting the one or more fully decomposed organic metal complexes to catalytically active metal.

In a further embodiment of the third aspect prior to treatment of the support with one or more catalytic metal precursors deposited thereon with one or more organic compounds the support with one or more catalytic metal precursors deposited thereon may be thermally treated by calcinations or pyrolysis. In a further embodiment of this aspect steps a) and b) may be reversed; the support may be treated in a first step with one or more organic compounds and the support with one or more organic compounds deposited thereon may be treated with a compound, or salt, of one or more catalytically active metals to form one or more organic complexes on the support, followed by full decomposition of the one or more organic complexes and conversion to catalytically active metal. In all embodiments of the third aspect the conversion to catalytically active metal may be carried out under reducing conditions e.g. in the presence of a source of hydrogen or CO. The organic compounds are preferably nitrogen containing organic compounds. In the third aspect of the present invention either the treatment with one or more organic compounds or the treatment with one or more compounds, or salts, of one or more catalytically active metals may be omitted if either of these compounds is introduced to the support during its preparation or synthesis.

In a fourth aspect the invention provides a process for the manufacture of a catalyst which comprises
a) preparing a support having one or more organic complexes of one or more catalytically active metals deposited thereon;
b) fully decomposing the one or more organic metal complexes deposited thereon; and
c) converting the one or more fully decomposed organic metal complexes to catalytically active metal.

In the third and fourth aspects the separate conversion step may be omitted if the full decomposition of the organic complex is undertaken under conditions where the fully decomposed organic complex is converted to catalytically active metal such as when the full decomposition is undertaken under reducing conditions e.g. in the presence of a source of hydrogen or CO.

In the first and fourth aspects of the present invention the first stage of the process may be achieved by formation of one or more organic complexes during the manufacture or synthesis of the support material. Alternatively the individual components required to form the complex may be incorporated into or within the support during its manufacture or synthesis, with formation of the organic complex occurring during a subsequent process step e.g. such as thermal treatment of such a support incorporating the components.

In a fifth aspect the invention also provides for a catalyst comprising one or more catalytically active metals deposited on one or more support materials wherein the total metal dispersion is 45% or more and the metal dispersion relating to a strongly chemisorbed component of the total metal dispersion is 20% or greater.

In a sixth aspect of the present invention there is provided a catalyst precursor comprising at least one support material and at least one source of one or more catalytically active metals deposited on the support material, wherein the source of one or more catalytically active metals is the decomposition product of one or more metal containing organic complexes. The catalyst precursor may be present as an intermediate in the processes of any one of the first to fourth aspects of the present invention after the full or partial decomposition of the organic complex. The catalyst precursor of this aspect of the invention is distinct from the catalytic metal precursors of the second and third aspects of the present invention; in each case in the second and third aspects the catalytic metal precursor precedes the formation of the catalyst precursor.

In a seventh aspect the present invention provides for a process for the production of $C_5+$ liquid hydrocarbons from a hydrogen and carbon monoxide synthesis gas by contact of the said gas at reaction conditions with a catalyst, wherein the catalyst is manufactured according to the first, second, third or fourth aspects of the present invention or is a catalyst according to the fifth or sixth aspect of the present invention.

In an eighth aspect of the present invention there is provided a method for the removal of sulfur from a mixture comprising one or more organic compounds and one or more sulfur containing compounds, in which method the mixture is contacted with one or more materials comprising active metal dispersed on an inorganic support and prepared using a process according to the first, second, third or fourth aspects of the present invention or a material according to the fifth or sixth aspect of the present invention, under such conditions that sulfur is adsorbed onto the material comprising active metal dispersed on an inorganic support. A preferred embodiment of this aspect is where the conditions selected are the normal conditions for Sulfur Trim treatment in the absence of added hydrogen.

BRIEF DESCRIPTION OF THE DRAWINGS

The present invention will be better understood by reference to the Detailed Description of the Invention when taken together with the attached drawings wherein.

DETAILED DESCRIPTION OF THE INVENTION

Figure 1:
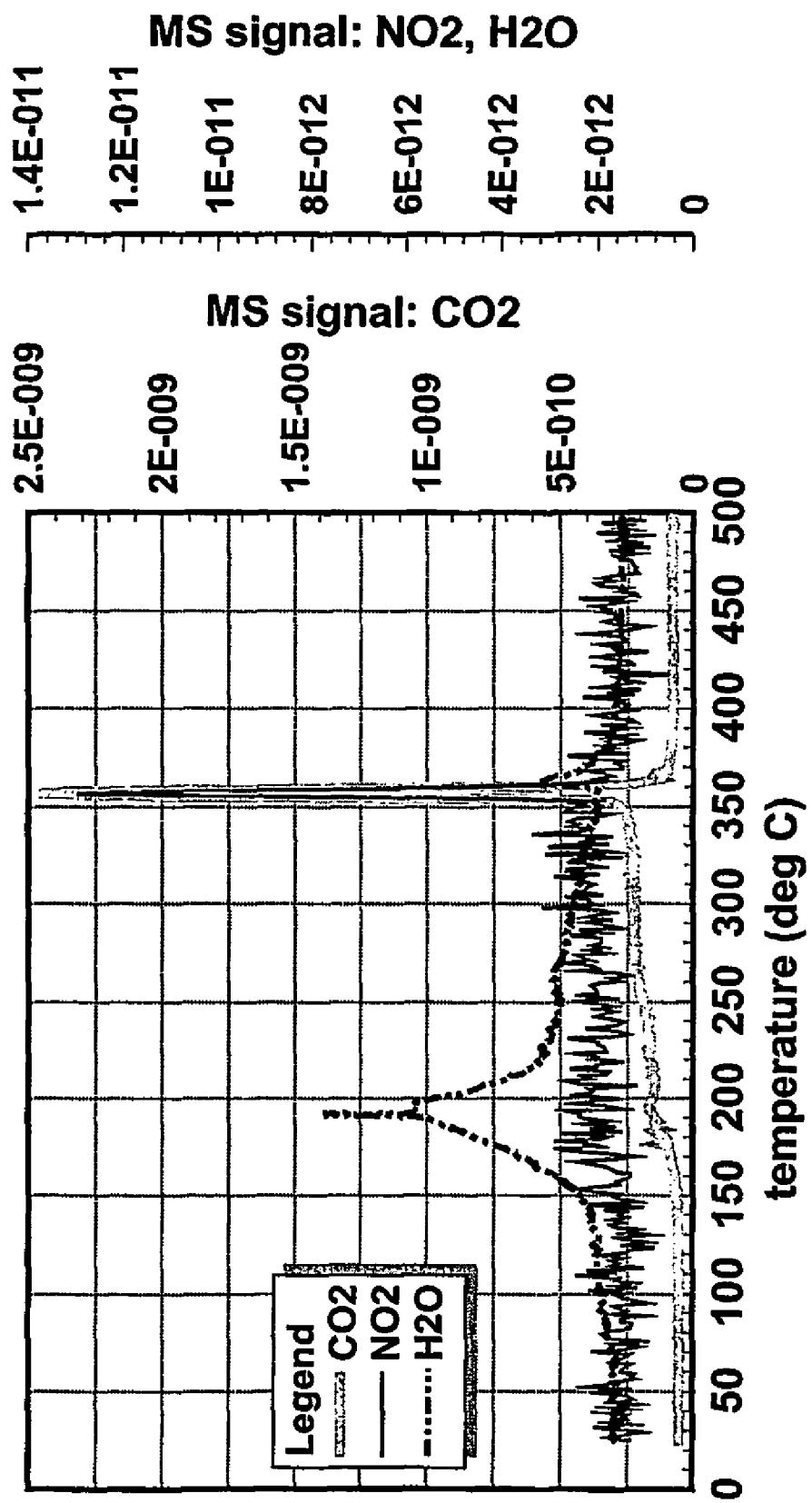
FIG. 1 shows a quadrapole mass spectrum of the product of Example 7 heated in air at 4 deg/min.

The various processes of the present invention have been found to be effective in producing supported metal catalysts with good levels of metal dispersion and distribution of the catalytically active metal in the final catalyst. An important feature of the processes of the present invention is the selection of the components used in the preparation of the supported metal catalysts and the sequence of process steps used in arriving at the final catalyst composition.

In all aspects of the present invention the processes may utilize a wide variety of inorganic support materials in preparation of the catalysts. These materials may be refractory inorganic oxides and may be selected from a wide variety of porous and non-porous support materials well known in the art. These include but are not limited to all forms of alumina, especially gamma alumina, all forms of silica, all forms of $TiO_2$ (both anatase and rutile or mixtures thereof), $ZrO_2$, activated carbon, silicon carbide, magnesium oxide, zinc oxide and similar metal oxides. The supports may be any combination or mixture of two or more of these materials. The exact nature of the support material used will depend on the proposed use of the catalyst. In all aspects of the present invention the most preferred supports are amorphous supports. Particularly preferred supports are silica supports especially supports comprising amorphous silica. In relation to the seventh aspect of the present invention one preferred support is a titanium oxide support modified with zirconium dioxide. A further class of preferred supports in all aspects of the present invention are porous supports especially supports having mesopores, macropores and mixtures thereof.

For the purposes of the present invention, the terms "macropores" and "mesopores" are used as they are defined in Pure Appl. Chem., 45 (1976), 79, namely as pores whose diameter is above 50 nm (macropores) or whose diameter is from 2 nm and 50 nm (mesopores).

In all aspects of the present invention the support may be a molecular sieve material such as for example a zeolite or zeolite like material. As molecular sieves there may be mentioned silicates, aluminosilicates, aluminophosphates, silicoaluminophosphates, metalloaluminophosphates, metalloaluminophosphosilicates, or a stannosilicates. The preferred molecular sieve as catalyst support will depend on the chosen application such as for example separations, catalytic applications, and combined reaction and separation applications. These are many known ways to tailor the properties of the molecular sieves, for example, structure type, chemical composition, ion-exchange, and activation procedures. Representative examples are molecular sieves/zeolites of the structure types AFI, AEL, BEA, CHA, EUO, FAU, FER, KFI, LTA, LTL, MAZ, MOR, MEL, MTW, OFF, TON and MFI. Some of these materials while not being true zeolites are frequently referred to in the literature as such, and this term will be used broadly in the specification below to include such materials.

One class of molecular sieve material that may be used as catalyst supports in all aspects of the present invention are those materials that may be synthesized using amphiphilic compounds as directing agents. Examples of such materials are described in U.S. Pat. No. 5,250,282, the whole contents of which are hereby incorporated by reference. Examples of amphiphilic compounds are also provided in Winsor, Chemical Reviews, 68(1), 1968. Other suitable molecular sieve materials of this type are also described in "Review of Ordered Mesoporous Materials", U. Ciesla and F. Schuth, Microporous and Mesoporous Materials, 27, (1999), 131-49. Such materials include but are not limited to materials designated as SBA (Santa Barbara) such as SBA-2, SBA-15 and SBA-16, materials designated as FSM (Folding Sheet Mechanism) such as FSM-16 and KSW-2, materials designated as MSU (Michigan State) such as MSU-S and MSU-X, materials designated as TMS or Transition Metal Sieves, materials designated as FMMS or functionalized monolayers on mesoporous supports and materials designated as APM or Acid Prepared Mesostructure. Particularly preferred crystalline molecular sieve materials of this class are the silicate or aluminosilicate mesoporous molecular sieve materials designated as M41S such as MCM-41, MCM-48, and MCM-50. These molecular sieves are described in detail in U.S. Pat. No. 5,098,684 (Kresge et al) and U.S. Pat. No. 5,102,643 to Kresge et al., both of which are incorporated herein by reference in their entirety. A particularly suitable sub-class of this family of materials for use in the present invention are the mesoporous silicas designated as MCM-41 and MCM-48. MCM-41 is particularly preferred and has a hexagonal arrangement of uniformly sized mesopores. MCM-41 molecular sieve materials are described in detail in U.S. Pat. No. 5,098,684, the whole contents of which are hereby incorporated by reference. The MCM-41 molecular sieves have a $SiO_2/Al_2O_3$ molar ratio when alumina is present that is greater than 100, more preferably greater than 200, and most preferably greater than 300. Other molecular sieves that may be used in all aspects of the present invention include those molecular sieves designated as MCM-1, MCM-2, MCM-3, MCM-4, MCM-5, MCM-9, MCM-10, MCM-14, MCM-22, and MCM-49.

The preferred ordered mesoporous materials for use in all aspects of the present invention are the ordered mesoporous silicas. The most preferred ordered mesoporous silicas are those designated as MCM-41.

Further examples of mesoporous materials that may be used in the processes of the present invention are the mesoporous silicas as described in and prepared according to U.S. Pat. No. 5,951,962, the disclosure of which is incorporated herein by reference in its entirety. In this reference mesoporous silica is prepared by converting a silica precursor in a water and polymer dispersion containing reaction medium. The preferred polymer dispersion is a cationic polymer.

High surface area mesoporous alumina solids may be also be used in preparing the catalyst supports for use in the processes of the present invention; such high surface area mesoporous alumina solids may be prepared according to the methods described in U.S. Pat. No. 6,238,701, the disclosure of which is incorporated herein in its entirety.

The support may consist of macroporous materials or materials that are both macroporous and mesoporous, such as those described in U.S. Pat. Nos. 5,936,126, 6,248,924 and 6,284,917 the disclosures of which are incorporated herein by reference in their entirety.

One or more of the support materials may be of mixed porosity and may be used in addition to other support materials that have either mesopores or macropores. These materials of mixed porosity may possess mesopores in addition to their macropores. Examples of such material are described in U.S. Pat. Nos. 6,248,924 and 6,284,917, the disclosures of which are incorporated herein by reference in their entirety.

In all aspects of the present invention the final catalyst may consist solely of one or more active metals deposited on the surfaces of one or more support materials. The catalyst in these embodiments is free of added inorganic binder. The supports with or without active metal deposited thereon may be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the can be extruded before drying or partially dried and then extruded. In these embodiments various extrusion or forming aids may be used in the extrusion or forming process along with one or more solvents.

In all aspects of the present invention the support material with one or more active metals deposited thereon may be formed into composites with inorganic binder or matrix materials that are resistant to the temperatures and other conditions employed in the catalytic processes envisaged for the catalyst. Such materials may also aid in the formation and manufacture of the final catalyst. Such materials include active and inactive materials and synthetic or naturally occurring zeolites as well as inorganic materials such as clays and/or oxides such as alumina, silica or silica-alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. These materials may be incorporated into naturally occurring clays, e.g., bentonite and kaolin, to improve the crush strength of the catalyst under commercial operating conditions and function as binders or matrices for the catalyst. The support comprising one or more catalytically active metals may be formed into a composition comprising the matrix material in amounts from 99:01 to 05:95 by weight, preferably from 99:01 to 10:90, more preferably from 99:01 to 20:80, and most preferably from 99:01 to 50:50, catalyst support to matrix material. Preferably, if used the additional matrix material is kept to a minimum typically less than 50 wt % of the combined weight of catalyst support and matrix material, ideally less than 40 wt %, preferably less than 30 wt %, more preferably less than 20 wt %, more preferably less than 15 wt %, most preferably less than 10 wt % and in a most preferred embodiment less than 5 wt %. Formation of the composition may be achieved by conventional means including mulling the materials together followed by extrusion of pelletizing into the desired finished catalyst particles. Ideally the additional matrix material is macroporous or is a material of mixed porosity i.e. both macroporous and mesoporous. The materials of mixed porosity may have a pore distribution in which from about 5 to about 50%, preferably from about 10 to about 45%, more preferably from about 10 to about 30 and in particular from about 15 to about 25%, of the pore volume is formed by macropores having pore diameters in the range from about 50 nm to about 10,000 nm and from about 50 to about 95%, preferably from about 55 to about 90%, more preferably from about 70 to about 90% and in particular from about 75 to about 85%, of the pore volume is formed by mesopores having a pore diameter of from about 2 to about 50 nm where in each case the sum of the pore volumes adds up to 100%.

In all aspects of the present invention the processes may be used to manufacture catalysts that are suitable for conducting carbon monoxide hydrogenation reactions especially Fischer-Tropsch reactions. In these embodiments a wide variety of support materials may be utilized such as those described above. Preferred support materials are titanium dioxide (both anatase and rutile), silica, silica-alumina, alumina and mixtures of titanium dioxide and zirconium dioxide. Supports comprising mixtures of titanium dioxide and zirconium dioxide are preferred. In a preferred embodiment the titanium dioxide is first washed to ensure that it is substantially chloride free and is then impregnated with a solution of a zirconium dioxide precursor such as $ZrO(NO_3)_2 \cdot 4H_2O$, optionally dried and calcined to form the $ZrO_2/TiO_2$ support. The final support may comprise up to 50 wt % zirconium dioxide, preferably up to 35 wt %, more preferably up to 20 wt %, even more preferably up to 10 wt % and most preferably within the range of 0.1 to 5 wt % of zirconium dioxide based on the total weight of the support. In addition to the support additional components are often used such as promoters or modifiers. Preferred examples of such materials are rhenium, ruthenium, hafnium, zirconium, titanium, chromium, thoria and copper etc. A particularly preferred promoter or modifier is rhenium, which exhibits important properties during calcination of the catalyst after deposition of the one or more catalytically active metals especially and preferably when one of these metals is cobalt. During the calcination stage the rhenium assists in ensuring that the cobalt is highly dispersed and it also helps to preserve the cobalt oxide formed in a highly dispersed state. A further benefit is that the rhenium lowers the temperature of reduction of the cobalt oxide to its zero valence state, which is its most catalytically active state; in this way rhenium makes it easier to more fully reduce the cobalt. One problem with the use of rhenium in these catalysts is that it is an expensive material. Therefore, there exists a need for means to achieve good cobalt dispersion in these catalysts whilst at the same time reducing or eliminating the amount of rhenium needed to achieve full activity of the catalyst. It has been found that if the processes of the present invention according to the first, second, third or fourth aspects are used it is possible to manufacture Fischer-Tropsch catalysts with good cobalt dispersion using reduced amounts of rhenium and/or to achieve higher levels of cobalt dispersion at any given level of rhenium. When the process used to manufacture a Fischer-Tropsch catalyst is in accordance with the first aspect of the present invention the organic complex is formed from one or more catalytically active metals and one or more nitrogen containing compounds other than those containing carboxylic acid functionality such as amino acids. Suitable nitrogen containing compounds include amines as described below. As an alternative to cobalt or in addition to cobalt other catalytically active metals may be used in preparing the catalyst such as other iron group metals and copper. When the catalysts of the present invention are for use as a Fischer-Tropsch catalyst, the titania support with or without zirconium dioxide may be used in combination with an inorganic binder such as alumina, silica or mixtures of alumina and silica. In this embodiment it is within the scope of the present invention to form the organic complex on the primary catalyst support i.e. without binder and before mixing with any binder or to from the organic complex on the support in admixture with one or more binder materials.

In all aspects of the present invention the processes may be used to manufacture catalysts that are suitable for the removal of organosulfur contaminants from hydrocarbon streams. The catalysts of the present invention may be used in the absence of hydrogen to remove sulfur species from a hydrocarbon stream. In such applications the level of metal dispersion in the catalyst is a critical factor in the effectiveness of the catalyst in removing the sulfur species. It has been found that highly effective sulfur adsorption catalysts may be obtained by using the processes according to the first, second, third and fourth aspects of the present invention. By using these processes it has been possible to highly disperse metals with sulfur adsorption activity on suitable supports. In these embodiments of the present invention a wide variety of support materials may be utilized such as those described above. A preferred support material is silica. In addition a wide variety of active metals suitable for sulfur treatment catalysts may be used; the preferred active metal is nickel. In these embodiments although the catalyst may be prepared according to the first, second, third or fourth aspect of the present invention it is preferred that the catalyst is manufactured according to the fourth aspect of the present invention. A preferred application is the removal sulfur in a process referred to in the art as Sulfur Trim.

In all aspects of the present invention the processes produce a final catalyst that comprises one or more active metals deposited on one or more support materials. A wide variety of active metals may be used in all aspects of the present invention. The choice of active metal is dependent on the intended use of the final catalyst and such correlations between active metal and catalyst use are well known in the art. In all aspects of the present invention examples of active metals that may be used include but are not limited to one or more of the following: Group 1 (Group IA) such as Li, Na or K; Group 2 (Group IIA) such as Mg, Ca and Sr; Group 3 (Group IIIA, IIIB) such as Sc, Y and La; Group 4 (Group IVA, IVB) such as Ti, Zr and Hf; Group 5 (Group VA, VB) such as V, Nb and Ta; Group 6 (Group VIA, VIB) such as Cr, Mo and W; Group 7 (VIIA, VIIB) such as Mn, Tc, and Re; Groups 8, 9 and 10 (Group VIII, VIIIA) such as Fe, Ru, Os, Co, Rh, Ir, Ni, Pd, and Pt; Group 11 (Group IB) such as Cu, Ag, and Au; Group 12 (Group IIB) such as Zn; Group 13 (Group IIIA, IIIB) such as Ga and In; and Group 14 (Group IVA, IVB) such as Ge and Sn. Preference is given to using copper, platinum, rhodium, palladium, cobalt, iron, nickel or ruthenium or a mixture of two or more thereof as active metal. A particular preference is given to using ruthenium, nickel, or cobalt or mixtures of two or more thereof. A particularly preferred active metal is ruthenium.

The content of the metal component will vary according to its catalytic activity and the proposed use of the catalyst. Thus, the highly active noble metals may be used in smaller amounts than the less active base metals. For example, about 1 wt. percent or less or ruthenium, palladium or platinum will be effective. The metal component may exceed about 30 percent in a monolayer.

When the active metal is a highly active noble metal its content in the catalyst in all aspects of the present invention is generally from about 0.01 to about 30% by weight, preferably from about 0.01 to about 20% by weight and in particular from about 0.1 to about 10% by weight, more preferably 1 to 5% by weight in each case based on the total weight of the catalyst used. One preferred catalyst in all aspects of the present invention is one that comprises ruthenium alone or in combination with one or more additional active metals at a total content of less than 5% by weight of active metal and preferably at a total content of less than 2% by weight of active metal. Preferably the content of ruthenium is from about 0.01 to 2%, more preferably 0.1 to 1% by weight of the total catalyst.

When the active metal is not particularly active or given the nature of the proposed application, such as in sulfur removal, high levels are required, in all aspects of the present invention the active metal may be present at levels of 10 wt % or more, preferably 15 wt % or more, more preferably 20 wt % or more and most preferably within the range of 15 to 45 wt % based on the total weight of catalyst used.

In all aspects of the present invention the catalyst is manufactured via a process in which a support is provided with one or more catalytically active metal sites through the use of a specific sequence of process steps. In all aspects the process has as a first or intermediate stage the formation of one or more organic complexes. In the first and fourth aspects of the present invention the formation of the organic complex may be achieved through the simultaneous application of the one or more compounds or salts of the catalytically active metals with, preferably in a admixture with, one or more organic compounds capable of forming a complex with the one or more metals or salts or compounds of the metals. Alternatively in the first and fourth aspects the one or more organic complexes may be formed during the manufacture or synthesis of the support; in this embodiment the support comprising organic complex formed in-situ is used in the process of the first and fourth aspects. In an alternative embodiment the components required to form the organic complex are incorporated into or within the support during its manufacture or synthesis with formation of the organic complex occurring during a subsequent process step such as thermal treatment of the support comprising the components. In the second and third aspects of the present invention the organic complex is formed in two distinct stages, the first being deposition of a salt or compound of one or more catalytically active metals and the second stage being the application of one or more organic compounds capable of forming a complex with the one or more metals or salts or compounds of the metals. In the second and third aspects it is also possible to reverse these two stages with deposition of the organic compound preceding deposition of the salts or compounds of the metals, although this stage inversion in relation to the second and third aspects is not preferred. In the second and third aspects the stage requiring either the deposition of a salt or compound of one or more catalytically active metals, or the stage requiring the deposition of one or more organic compounds capable of forming the complex, may be omitted if the compounds of either stage have been introduced into the support used during its manufacture or synthesis.

In one embodiment of the first and fourth aspects a compound, or salt, of one or more catalytically active metals is combined with one or more organic compounds to form a mixture which is then contacted with a support to deposit the organic complex. In this embodiment the complex may be formed on formation of the mixture or may be formed after contact with the support and after removal of any solvent or solvents used during formation of the mixture. In a further embodiment of these aspects one or more organic compounds and a compound, or salt, or one or more catalytically active metals are contacted simultaneously with the support to form the organic complex. In yet a further embodiment of these aspects a suitable organic complex of the desired metal may be synthesised and applied to the support via solution of the complex in a suitable solvent for the complex. In yet a further embodiment of the first and fourth aspects the organic complex may be formed in-situ during the manufacture or synthesis of the support material or from components required for formation of the organic complex, that have been incorporated into or within the support during its manufacture or synthesis.

In the second and third aspects the support is first contacted with a compound, or salt, of one or more catalytically active metals followed by treatment with one or more organic compounds to form the organic complex on the support. In an alternative embodiment the support is first contacted with one or more organic compounds followed by treatment with a compound, or salt, or one or more catalytically active metals to form the organic complex on the support. In either embodiment the compounds may be introduced during manufacture or synthesis of the support.

In the second and third aspects of the present invention the one or more catalytically active metals may be exchanged onto the support material, impregnated into it or physically admixed with it. The application of the individual components or mixture of components may be achieved by steeping the support in an aqueous metal salt solution, or a solution in a suitable solvent of a compound of the metal. In the first and fourth aspects of the present invention a mixture of a compound, or salt, of one or more catalytically active metals with one or more organic compounds may be brought into contact with the support to form the organic complex. In all aspects the application of one or more of the components or mixtures of components may be brought into contact with the support materials using such methods as dipping, spraying, slurry techniques or any other suitable method. The preferred methods are impregnation of the support using such techniques as incipient wetness or slurry techniques. In all aspect of the present invention suitable metal salts for preparing the metal salt solutions of for use in preparing the mixtures are for example nitrates, nitrosyl nitrates, halides, carbonates, carboxylates, acetylacetonates, chloro complexes, nitrito complexes or ammine complexes of the corresponding metals, with preference being given to the nitrates and nitrosyl nitrates and most preferably the nitrosyl nitrates. In all aspects of the present invention the organic compounds are present in addition to the normal counter ion or moiety of the salt or compound of the active metal. However, this may not be the case where the organic complex is prepared in a separate procedure for use in the processes of the present invention; in these circumstances the original counter-ions or moieties for the salt or compound of the metal will have been removed from the purified organic metal complex. The original counter ion may also be absent when the organic complex is prepared in-situ during the manufacture or synthesis of the support or where the components required to form the complex are incorporated into or within the support during its manufacture or synthesis; in these embodiments the counter-ion to the metal may be provided by a charge associated with the support structure or the organic moiety or moieties of the organic complex. When Pt is the active metal it is preferred that it is not complexed with the organic compound as its nitrate salt, preferably it is complexed as a chloride or hydroxide salt.

In all aspects of the present invention catalysts that have a plurality of active metals applied to the support may have these metals applied simultaneously using the various processes of the present invention or the process steps may be repeated to apply the metals in sequence.

In all aspects of the present invention any organic compounds that are capable of forming organic complexes with the one or more catalytically active metals may be used. Typically these will be organic compounds that are capable of forming complexes that are stable under the conditions that are normally used for depositing catalytically active metals. Ideally, the organic compounds are selected to provide metal organic complexes that are stable under the conditions normally used for drying catalyst supports after impregnation with one or more catalytically active metals. Suitable organic compounds are well known in the art of transition metal chemistry and include such organic compounds as organic chelating agents, organic monodentate, bidentate and polydentate ligands commonly used in the preparation of transition metal coordination complexes. In a number of such complexes one or more ligands being covalently bonded molecules and/or ions may be present in the complex. In all aspects of the present invention the organic compound may be one or more organic compounds used in the manufacture of the support or present during its synthesis, such as for example organic templates used in the manufacture of molecular sieve supports.

In the process of the present invention particularly suitable organic compounds are compounds that contain one or more amino groups such as amines or amino acids, a particularly preferred group of organic compounds are those that contain both amino and alcohol groups within the compound. In the case of Fischer-Tropsch catalysts prepared according to the process of the fourth aspect the preferred organic compounds are nitrogen-containing compounds that are free of carboxylic acid functionality so amino acids are not preferred and are excluded from this embodiment. In this embodiment the preferred organic compounds are amines that are free of carboxylic acid functionality.

In all aspects of the present invention the preferred organic compounds contain one or more amino groups. Such compounds having one or more amino groups may be aliphatic amines, cycloaliphatic amines, aralkyl amines and alkylaryl amines. These may be primary, secondary and tertiary amines. They may also be quaternary ammonium salts with a counter ion. It is preferred that the nitrogen-containing compound is one or more primary, secondary or tertiary amine, preferably one or more aliphatic amines and most preferably one or more alcohol groups such as for example those found in hydroxyalkylamines.

In one embodiment, the nitrogen-containing compound used according to the present invention has the following general formula:

$$NR^1R^2R^3 \qquad (I)$$

wherein $R^1$, $R^2$ and $R^3$ independently are one or more of the following groups: $C_1$-$C_{50}$-alkyl, $C_3$-$C_{50}$-cycloalkyl, aromatic, alkyl substituted aromatic, such as $C_1$-$C_{50}$-alkyl substituted aromatic, aromatic substituted aliphatic moieties such as $C_1$-$C_{50}$-alkylene moieties substituted with one or more aromatic groups, $C_1$-$C_{50}$-hydroxyalkyl, amino- and/or hydroxyl-substituted $C_1$-$C_{50}$-alkyl, alkoxyalkyl such as $C_2$-$C_{50}$-alkoxyalkyl, dialkylaminoalkyl such as $C_3$-$C_{50}$-dialkylaminoalkyl, alkylaminoalkyl such as $C_2$-$C_{50}$-alkylaminoalkyl; heterocyclic, aromatic heterocyclic, alkyl substituted heterocyclic and alkyl substituted aromatic heterocyclic, such as $C_1$-$C_{50}$-alkyl substituted heterocyclic and aromatic heterocyclic compounds, and heterocyclic substituted aliphatic moieties such as $C_1$-$C_{50}$-alkylene moieties substituted with one or more aromatic groups. In addition, $R^1$ and $R^2$ may independently be hydrogen. In another embodiment, $R^1$ and $R^2$ may form, with the nitrogen atom, a nitrogen-containing heterocycle, aromatic heterocycle, alkyl substituted heterocycle or alkyl substituted aromatic heterocycle.

Examples of alkyl groups include; methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, n-decyl, 2-n-propyl-n-heptyl, n-tridecyl, 2-n-butyl-n-nonyl and 3-n-butyl-n-nonyl, particularly preferably ethyl, isopropyl, 2-ethylhexyl, n-decyl, 2-n-propyl-n-heptyl, n-tridecyl, 2-n-butyl-n-nonyl and 3-n-butyl-n-nonyl, and $C_{40}$-$C_{200}$-alkyl such as polybutyl, polyisobutyl, polypropyl, polyisopropyl and polyethyl. The most preferred aliphatic amines are aliphatic amines having one or more alkyl groups having 1 to 20 carbon atoms and more preferably 2 to 14 carbon atoms.

Examples of cycloalkyl groups include $C_3$-$C_{12}$-cycloalkyl, preferably $C_3$-$C_8$-cycloalkyl such as cyclopropyl, cyclobutyl, cyclopentyl, cyclohexyl, cycloheptyl and cyclooctyl.

Examples of aromatic groups include; phenyl, 1-naphthyl, 2-naphthyl, 1-anthryl, 2-anthryl and 9-anthryl, 1-phenanthryl, 2-phenanthryl, 3-phenanthryl, 4-phenanthryl and 9-phenanthryl.

Examples of alkyl substituted aromatic groups include $C_7$-$C_{50}$ alkyl aromatic groups, preferably $C_7$-$C_{40}$-alkylphenyl such as 2-nonylphenyl, 3-nonylphenyl, 4 nonylphenyl, 2-decylphenyl, 3-decylphenyl, 4-decylphenyl, 2,3-dinonylphenyl, 2,4-dinonylphenyl, 2,5-dinonylphenyl, 3,4-dinonylphenyl, 3,5-dinonylphenyl, 2,3-didecylphenyl, 2,4-didecylphenyl, 2,5-didecylphenyl, 3,4-didecylphenyl and 3,5-didecylphenyl, more preferably $C_7$-$C_{12}$ alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl.

Examples of aromatic substituted aliphatic moieties include $C_7$-$C_{50}$ alkylene moieties substituted with one or more aromatic substituents, preferably $C_7$-$C_{12}$-phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl.

Examples of hydroxyalkyl groups include amines having one or more $C_1$-$C_{50}$-hydroxyalkyl groups, preferably $C_1$-$C_8$-hydroxyalkyl groups, particularly preferably $C_1$-$C_4$-hydroxyalkyl groups such as hydroxymethyl, 1-hydroxyethyl, 2-hydroxyethyl, 1-hydroxy-n-propyl, 2-hydroxy-n-propyl, 3-hydroxy-n-propyl and 1-hydroxy-methyl-ethyl. Particularly preferred hydroxyalkyl group containing nitrogen compounds include the mon-, di-, and tri-, substituted aliphatic hydroxyalkylamines such as methanolamine, di-methanolamine, tri-methanolamine, ethanolamine, di-ethanolamine, tri-ethanolamine, butanolamine, di-butanolamine, tri-butanolamine, propanolamine, di-propanolamine, and tri-propanolamine. Also preferred are N,N,-dialkyl-ethanolamines, N-alkyl-diethanolamines, N-alkyl-ethanolamines, N,N,-dialkyl-methanolamines, N-alkyl-dimethanolamines, N-alkyl-methanolamines and equivalent propanolamines, butanolamines, hexanolamines and heptanolamines. In these alkanolamines the N-alkyl group may be a hydrocarbon or substituted hydrocarbon group containing from 1 to 50 carbon atoms, preferably 1 to 8 carbon atoms and most preferably 1 to 4 carbons atoms such as methyl, ethyl, n-propyl, isopropyl, n-butyl, isobutyl, n-pentyl, isopentyl, n-hexyl, isohexyl etc.

Examples of amino- and hydroxyalkyl groups include $C_1$-$C_{50}$-alkyl, preferably amino- and/or hydroxyl-substituted $C_1$-$C_8$-alkyl, particularly preferably amino and/or hydroxyl-substituted $C_1$-$C_4$-alkyl such as N-(hydroxyethyl)aminoethyl and N-(aminoethyl)aminoethyl.

Examples of alkoxyalkyl groups include $C_2$-$C_{50}$-alkoxyalkyl, preferably $C_2$-$C_{20}$-alkoxyalkyl, particularly preferably $C_2$-$C_8$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly preferably $C_2$-$C_4$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl.

Examples of dialkylamino groups include $C_3$-$C_{50}$-dialkylaminoalkyl, preferably $C_3$-$C_{20}$-dialkylaminoalkyl, particularly preferably $C_3$-$C_{10}$-dialkylaminoalkyl such as dimethylaminomethyl, dimethylaminoethyl, diethylaminoethyl, di-n-propylaminoethyl and diisopropylaminoethyl.

Examples of alkylaminoalkyl groups include $C_2$-$C_{50}$-alkylaminoalkyl, preferably $C_2$-$C_{20}$-alkylaminoalkyl, particularly preferably $C_2$-$C_8$-alkylaminoalkyl such as methylaminomethyl, methylaminoethyl, ethylaminomethyl, ethylaminoethyl and iso-propylaminoethyl.

Examples of aromatic heterocycles include 2-pyridinyl, 3-pyridinyl, 4-pyridinyl, pyrazinyl, 3-pyrrolyl, 2-imidazolyl, 2-furanyl and 3-furanyl. Examples of alkyl substituted aromatic heterocycles include $C_4$-$C_{50}$-mono-hetarylalkyl, such as 2-pyridylmethyl, 2-furanyl-methyl, 3-pyrrolylmethyl and 2-imidazolylmethyl, and $C_4$-$C_{50}$-alkylhetaryl such as 2-methyl-3-pyridinyl, 4,5-dimethyl-2-imidazolyl, 3-methyl-2-furanyl and 5-methyl-2-pyrazinyl.

Examples of alkylaminoalkyl groups include $C_2$-$C_{50}$-alkylaminoalkyl, preferably $C_2$-$C_{16}$-alkylaminoalkyl such as methylaminomethyl, methylaminoethyl, ethylaminomethyl, ethylaminoethyl and isopropylaminoethyl.

Examples of dialkylaminoalkyl groups include $C_3$-$C_{50}$-dialkylaminoalkyl, preferably $C_3$-$C_{16}$-dialkylaminoalkyl such as dimethylaminomethyl, dimethylaminoethyl, diethylaminoethyl, di-n-propylaminoethyl and diisopropylaminoethyl.

Examples of heterocyclic compounds, include pyridine, pyrrole, imidazole, oxazole, thiazole, pyrazole, 3-pyrroline, pyrrolidine, pyrimidine, and substituted examples of these heterocyclic compounds. Examples of organonitrile compounds include acrylonitrile, alkyl nitriles such as for example methyl nitrile, and ethyl nitrile.

Suitable amino acids include natural and synthetic amino acids. The natural amino acids include all isomers of the following: alanine, arginine, asparagines, aspartic acid, cysteine, cystine, 3,5-dibromotyrosine, 3,5, diiodotyrosine, glutamic acid, glutamine, glycine, histidine, hydroxylysine, hydroxyproline, isoleucine, leucine, lysine, methionine, phenylalanine, proline, serine, threonine, thyroxine, tryptophane, tyrosine and valine, a particularly preferred amino acid is L-arginine. These amino acid compounds are not used as the organic compound for the preparation of Fischer-Tropsch catalyst according to the process of aspect four of the present invention.

In all aspects especially the first and second aspects of the present invention the preferred organic compounds for forming the organic complex are organic nitrogen containing compounds, more preferably amines, and more preferably amines containing one or more alcohol groups.

In all aspects of the present invention the organic compound may be introduced into the manufacture or synthesis of the support. The organic compound may be an organic template as used in the synthesis of the support when the support is a molecular sieve. Such organic templates are well known in the art and are preferably nitrogen containing organic templates, especially nitrogen containing organic templates, which further comprise hydroxyl functionality. The organic compound may be introduced in addition to any organic template during the manufacture or synthesis of the support. In all aspects when either or all components for the preparation of the organic complex are incorporated into or within the support or the organic complex itself is incorporated into or within the support, the support may be used in the green state.

The organic compound may be used at any suitable level in relation to the amount of salt or compound of the catalytically active metal. The organic compound may be present in excess of that required to form the organic complex. Ideally the compounds are used at an appropriate mole ratio to convert all of the salt or compound of the catalytically active metal to one or more organic complexes. This may be a molar ratio of 1:1 or higher depending on the capacity of the metal to complex with the organic compound, the capacity of the organic compound to complex with the metal and the presence of other complexing ligands such as monodentate ligands. However it is possible to use levels of organic compound which are insufficient to complex with all of the catalytically active metal; in these circumstances not all of the metal is converted to organic complex and the resulting catalyst may contain catalytically active metal sites that have been derived from complexed and non-complexed metal intermediates. Ideally, the mole ratio of organic compound to catalytically active metal is within the molar ratio range of 0.1:1 to 40:1, preferably, 0.1:1 to 30:1, more preferably 0.2:1 to 25:1, even more preferably 0.5:1 to 10:1, most preferably 0.5:1 to 5:1. Excess organic compound may be present when the organic compound is incorporated into or within the support during manufacture or synthesis of the support.

When the complex is formed in a mixture before contact with the support as in the first and fourth aspects of the present invention the mixture is usually and preferably formed in combination with a solvent, which may be water or an organic solvent or a mixture of water and solvent. The amount of solvent used may vary within wide ranges but is typically sufficient to ensure that the mixture may be effectively contacted with the support so as to wet the support and when the support is porous to allow penetration of the mixture into the porous support. Typically the salt or compound of one or more catalytically active metals and the organic compound(s) are used in amounts which depending on their form allow the required mole ratios indicated above to be achieved in the mixture. The remainder of the mixture comprises one or more solvents which may be present in an amount from 1 to 99 wt % of the weight of the total mixture, preferably 5 to 90 wt % of the weight of the total mixture, more preferably 5 to 80 wt % of the weight of the total mixture, even more preferably 10 to 70 wt % of the weight of the total mixture and most preferably 10 to 65 wt % of the weight of the total mixture. Additional solvents may also be used in the second and third aspects of the present invention in order to facilitate application of one or more of the components required to manufacture the catalyst.

All aspects especially in the first and fourth aspects after formation of the organic complex on the support the support may and preferably is dried to remove most of the solvent and/or water present during formation of the complex. Drying may be achieved under ambient conditions such as room temperature or this may be achieved at elevated temperatures, preferably drying is at a temperature from 100 to 150° C. Preferably, little or no decomposition of the organic complex occurs during the drying phase and drying merely results in the removal of non-complexed volatile materials.

In the second and third aspects of the present invention the support may be dried after each or all deposition stages. Drying may be achieved under ambient conditions such as room temperature or this may be achieved at elevated temperatures, preferably drying is at a temperature from 100 to 150° C. Preferably, for the drying stage which follows formation of the complex little or no decomposition of the organic complex occurs during the drying phase and drying merely results in the removal of non-complexed volatile materials.

In the first and second aspects of the present invention once the support comprising one or more organic complexes has been prepared the support is treated so as to partially decompose the organic complex on the support. Although not wishing to be bound by any theory it is believed that this partial decomposition results in the formation in-situ of one or more precursors to the catalytically active metal sites. It is believed that it is, in part, the formation of these precursors and their subsequent conversion that ensures that in these aspects the final catalyst exhibits a high degree of catalytic activity and has high levels of metal dispersion within the catalyst. An important parameter in the activity of catalytically active metals is the form of the metal on the support and the level of dispersion of the metal on the support. The process of the present invention produces catalysts that comprise catalytically active metal sites that are relatively small and highly dispersed. In addition the level of dispersion is relatively stable.

In the third and fourth aspects of the present invention once the support comprising one or more organic complexes has been prepared the support is treated so as to fully decompose the organic complex on the support. Although not wishing to be bound by any theory it is believed that this full decomposition of the organic complex in these aspects results in the formation in-situ of one or more precursors to the catalytically active metal sites. It is believed that it is, in part, the formation of these precursors and their subsequent conversion that ensures that in these aspects the final catalyst exhibits a high degree of catalytic activity and has high levels of metal dispersion within the catalyst.

In all aspects of the present invention when reference is made to relatively small metal particles as active metal sites it is meant metal particles with an average particle size of 10 nm or less, preferably 8 nm or less, and most preferably 6 nm or less.

Chemisorption measurements are commonly used to estimate the size of supported metal catalysts and metal surface area. The general method for measuring metal surface area by chemisorption is described in J. Lemaitre et al., "Characterization of Heterogenous Catalysts", edited by Francis Delanney, Marcel Dekker, New York (1984), pp. 310-324. The total metal surface area is ideally within the range from 0.01 to 30 $m^2/g$, preferably from 0.05 to 25 $m^2/g$, more preferably from 0.05 to 20 $m^2/g$, even more preferably from 0.05 to 15 $m^2/g$, more preferably from 0.05 to 10 $m^2/g$, even more preferably from 0.05 to 5 $m^2/g$ and most preferably from 0.05 to 3 $m^2/g$ of the catalyst. From chemisorption measurements, the % dispersion (% of metal atoms that populate the surface of the metal particles) can be estimated since a properly chosen titrant used in the chemisorption measurements adsorbs only on metal atoms populating the surface. Consequently higher dispersion values indicate smaller particles with more of the metal atoms populating the surface. For many hydrogenation reactions, activity correlates with dispersion. The preferred method for determining metal dispersion is by using hydrogen as the chemisorption probe molecule under high vacuum static conditions as follows. The sample is held at a temperature of 40° C. and an 8-point isotherm (with pressures between 80 and 400 torr) is obtained using $H_2$ as the chemisorption probe molecule. The linear portion of this isotherm is extrapolated to zero pressure to obtain the total quantity of hydrogen chemisorbed; this is the combined dispersion. The sample is then evacuated at 40° C. to remove any weakly adsorbed hydrogen and the titration repeated to determine what is referred to as weak adsorption isotherm. The linear portion of this weak adsorption isotherm is extrapolated to zero pressure to obtain the quantity of weakly chemisorbed hydrogen. Subtraction of these two values for combined dispersion and weak dispersion yields the strongly held chemisorbed quantity. Thus this method provides values for the total metal dispersion, the dispersion due to weakly chemisorbed hydrogen and dispersion due to strongly chemisorbed hydrogen. The value for the strongly chemisorbed hydrogen is an accurate indication of metal dispersion. In many prior art references the metal dispersion figures provided are based on the total chemisorbed probe and are not split into strong and weak components. In the present invention it is preferred that the hydrogenation catalysts used have dispersion values relating to the strongly chemisorbed component in excess of 20% more preferably in excess of 25% and most preferably in excess of 30%. In addition total dispersion values in excess of 45% preferably in excess of 50%, more preferably in excess of 55%, and most preferably in excess of 60% are achieved. Preferably 40% or more of the total metal dispersion relates to the strongly chemisorbed component, more preferably 45% or more and most preferably 50% or more.

In the first and second aspects of the present invention the organic complex is at least partially decomposed. In the context of the present invention "partial decompositions" means that the chemical composition of the organic complex is varied; this may be due to a change in the structure of the organic complex or may be due to the chemical destruction of part of or a component of the complex. When the destruction is partial the method of destruction is selected to ensure that the removal of non-metal chemical species associated with the complex is incomplete. When the destruction is complete the only significant element of the complex remaining would be the one or more catalytically active metals as oxides when destruction is carried out under oxidizing conditions or the reduced metal when the destruction is carried out in the presence of hydrogen or other conditions that would convert the complex to catalytically active metal. There may also be residues such as carbon residues formed from decomposition of the organic complex. The partial decomposition is due to variations in structure and/or composition that do not normally occur under the drying conditions typically used in catalyst preparation methods. The changes of structure and/or composition under the conditions of the second stage may be detected and monitored using various analytical techniques that are well known in the art such as infra-red spectroscopy, mass spectroscopy, thermogravimetric analysis, gas or liquid chromatography and spectroscopy.

A variety of methods may be used to induce partial or full destruction of the organic complex. These include chemical methods such as chemically induced hydrolysis or decomposition such as by the treatment with acid or base or ozone or similar chemical active materials. Other methods for inducing full or partial decomposition include thermal methods such as pyrolysis and/or calcination, both of which are the preferred methods with particular preference being given to calcination. A further method is treatment with steam. In one embodiment the pyrolysis may be carried out in the presence of hydrogen; in this embodiment any subsequent treatment with hydrogen may be omitted. Other methods that may be used are those that would ensure that the organic complex is converted to catalytically active metal such as for example under reducing conditions in the presence of hydrogen and/or CO. In an alternative embodiment in relation to all aspects of the present invention the full or partial decomposition may be achieved by introducing the support comprising organic complex into the intended catalyzed process itself. In these embodiments the organic complex is decomposed under the process conditions of use if the support comprising organic complex is introduced directly into the catalyzed process or under the conditions used at any point of introduction of catalyst into the process plant such as the conditions in a catalyst regeneration unit or catalyst recycle unit. It is also envisaged that when decomposition is achieved in the process of use then the conversion of the fully or partially decomposed organic complex to catalytically active metal is also achieved in the same process either during the decomposition or subsequent to the decomposition in a separate conversion stage or unit where the conditions may be different from those of the process; such as those present in a catalyst regeneration or recycle unit. The destruction and conversion may be achieved in subsequent catalyst processing steps such as when the catalyst support comprising organic complex is formulated into a final catalyst composition that may comprise one or more binders and/or other formulated components. In these additional steps process conditions may be used that result in decomposition and/or conversion.

When calcination or pyrolysis is used as the method for full or partial decomposition of the organic complex the exact conditions used will depend on the nature of the complex and especially its thermal stability and decomposition profile under elevated temperature. By using thermogravimetric methods or mass spectroscopy linked with controlled thermal decomposition of the organic complex it is possible to determine at what temperature either under calcination conditions or pyrolysis conditions that initial decomposition and total decomposition of the organic complex occurs. This indicates the temperature range at which this partial decomposition stage should be undertaken or the minimum temperature that should be selected of full decomposition is required. Alternatively when analysed by infra-red spectroscopy it may be determined at what point in the treatment that a certain functional group is either removed from or formed in the organic complex; the temperature at which this occurs if below the total decomposition temperature may be selected as the temperature for the partial decomposition or if above the total decomposition temperature may be selected as the temperature for full decomposition. In the case where amines are used as the organic compound the temperature below which significant quantities of nitrogen oxides are produced may be selected as the temperature for treatment to induce partial decomposition. For other organic compounds it may be the temperature at which CO or $CO_2$ are removed from the complex. In the case of amines and especially amines containing hydroxyl groups or amino acids as the organic compound it may be the formation of new vibration bands that appear in the infra-red spectra at between 2100-2200 $cm^{-1}$ and tentatively assignable to complex carbon nitrogen species such as nitrites and isonitriles being present in the partially decomposed organic complex. Another method that may be used is where TGA analysis shows total weight loss of the organic complex; temperatures below total weight loss may be selected for partial decomposition and temperatures at or above the temperature for total weight loss may be selected for full decomposition.

In all aspects of the present invention when calcination is used to partially or fully decompose the organic complex the calcination temperatures used are typically within the range of 200 to 1000° C., preferably from 250 to 600° C. The exact temperature used will depend on whether or not full or partial decomposition of the organic complex is desired and will depend on the nature of the organic complex. Factors that may affect the decomposition temperature of the organic metal complex include the nature of the metal and/or organic compound within the complex. Another factor may be the nature of the counter-ion present when the metal is introduced in the form of a salt. Preferably when partial decomposition is required the support with the organic complex deposited thereon is calcined at a temperature that is less than the temperature as determined by TGA in air, at which total weight loss of the organic complex occurs. Preferably it is between 200° C. and the temperature at which total weight loss of the organic complex occurs. Preferably when full decomposition is required the support with the organic complex deposited thereon is calcined at a temperature that is at or above the temperature, as determined by TGA, at which total weight loss of the organic complex occurs. Preferably it is between the temperature at which total weight loss of the organic complex occurs and 1000° C. Under calcination conditions oxygen is present either as a component of an otherwise inert diluent or as a consequence of calcination being undertaken in air. When pyrolysis is used the pyrolysis may be undertaken in an inert atmosphere free of oxygen or in an atmosphere that also results in conversion to catalytically active metal such as a hydrogen or a CO containing atmosphere that may be and preferably is free of oxygen. When pyrolysis is used the organic complexes may decompose at higher temperatures than those observed under calcinations conditions. As with calcination the temperature, under pyrolysis conditions, for partial or full decomposition may be determined using a variety of methods of which TGA is preferred. Preferably when partial decomposition is required under pyrolysis conditions in an inert atmosphere or under hydrogen, the support with the organic complex deposited thereon is pyrolysed in an inert atmosphere or under hydrogen at a temperature that is less than the temperature as determined by TGA in an inert atmosphere or under hydrogen, at which total weight loss of the organic complex occurs. Preferably it is between 200° C. and the temperature at which total weight loss of the organic complex occurs under pyrolysis conditions in an inert atmosphere or under hydrogen. Preferably when full decomposition is required the supports with the organic complex deposited thereon are pyrolysed at a temperature that is at or above the temperature, as determined by TGA, at which total weight loss of the organic complex occurs under pyrolysis conditions in an inert atmosphere or under hydrogen. Preferably it is the between the temperature, under pyrolysis conditions in an inert atmosphere or under hydrogen, at which total weight loss of the organic complex occurs and 1000° C. Preferably the supports with the organic complex deposited thereon are pyrolysed in nitrogen or hydrogen at a temperature of less than 1000° C. The support comprising organic complex may be calcined or pyrolysed at the partial decomposition temperature for a period of time that is sufficient to ensure the partial decomposition of the organic complex occurs. Typically this will be for a period of at least 20 minutes, preferably at least 30, more preferably at least 45 mins and most preferably for 1 hour or more. Typically the period of time is 48 hours or less, preferably 24 hours or less and most preferably 12 hours or less. When full decomposition is required the support comprising organic complex may be calcined or pyrolysed at the full decomposition temperature for a period of time that is sufficient to ensure the full decomposition of the organic complex.

The support comprising the decomposition product of the organic complex is a new catalyst precursor according to the sixth aspect of the present invention. In a this aspect there is provided a catalyst precursor comprising at least one support material and at least one source of one or more catalytically active metals deposited on the support material, wherein the source of one or more catalytically active metals is the decomposition product of one or more metal containing organic complexes. In this aspect the source of one or more catalytically active metals is preferably the partially decomposed product of one or more metal containing organic complexes. In this aspect it is also preferred that the catalyst precursor exhibits dispersion values, when using hydrogen as the titrant, relating to the strongly chemisorbed component that are less than 1%, more preferably less than 0.75%, more preferably less than 0.5%, even more preferably less than 0.25% and most preferably 0%. The precursor of the sixth aspect may also exhibit unique absorption bands in their infra-red spectra; the precursors of the sixth aspect may comprise one or more infra-red absorption bands within the range 2100-2200 $cm^{-1}$ not present in the pre-decomposed organic complex. The precursor may also retain a significant proportion of the weight of the original organic complex; the precursor may retain between 10 and 95% by weight of the weight attributed to the organic complex after drying the support with complex formed thereon, the precursor preferably retains between 20 and 75% by weight of the weight of the original complex, more preferably it retains up to 60%, even more preferably up to 50%, and most preferably up to 40%. It is also a property of the precursor when the organic complex is partially decomposed that its reduction temperature to form the catalytically active metal is in excess of the normal reduction temperature required to reduce the fully oxidized metal complex to catalytically active metal, preferably it is at least 5% in excess, more preferably 10% in excess, even more preferably 15% in excess and most preferably 20% in excess of the normal reduction temperature. The catalysts of the fifth aspect and the process of all other aspects of the present invention may utilize one or more precursors according to the sixth aspect of the present invention. The catalyst precursor may be derived using the materials and compounds and process steps as described in relation to aspects 1 to 5 of the present invention e.g. support materials, organic compounds used to for the organic complex formation, metal salts and compounds used, methods of forming the organic complex, methods of full and partial decomposition of the organic complex and methods of drying etc.

In accordance with all aspects of the present invention after partial or full decomposition of the complex the partially decomposed or fully decomposed complex is converted to catalytically active metal. Preferably, the conversion is achieved via treatment of the partially or fully decomposed complex under conditions to reduce the partially or fully decomposed complex; is the presence of a reductant source. In preferred embodiments the reductant source is a source of hydrogen and/or carbon monoxide. In further embodiment in relation to all aspects the conversion my be achieved by introduction of the support comprising one or more fully or partially decomposed organic complexes into a process designed to use the final catalyst; in this embodiment the conversion occurs under the process conditions or the conditions present in a catalyst regeneration or recycle unit associated with the process. In a preferred embodiment this treatment is undertaken using conditions and methods normally used for the activation of catalysts. These conditions and methods are selected to ensure that the catalyst precursor is converted to catalytically active metal. In one embodiment the treatment with reductant e.g. source of hydrogen and/or CO is carried out by contacting the support comprising partially decomposed complex with a gas stream comprising reductant e.g. a source of hydrogen and/or CO at from 30 to 600° C., preferably from 100 to 550° C., even more preferably from 200 to 500° C., and most preferably from 200 to 450° C. When the reductant stream comprises free hydrogen it preferably consists of from 50 to 100% by volume of $H_2$ and from 0 to 50% by volume of $N_2$. The treatment may be carried our under a continuous flow of reductant e.g. source of hydrogen and/or CO under atmospheric pressure or under static conditions at elevated pressures up to 100 bar, preferably 1 to 90 bar, more preferably 1 to 20 bar. The activation may be undertaken for a period of up to 48 hours, preferably no more than 36 hours, more preferably less than 24 hours, and most preferably from 30 mins to 12 hours. In the first and second aspects preferably the support comprising partially decomposed complex is exposed to reductant e.g. source of hydrogen and/or CO at atmospheric pressure and the temperature raised at a rate of 2° C. min$^{-1}$ to the treatment temperature where reductant treatment is continued for a further 1 to 10 hours, preferably 2 to 8 hours and most preferably 3 to 6 hours. In the first and second aspects the exact temperature and time are selected to ensure that under the reductant treatment any residual partially decomposed organic complex is removed; therefore the reductant treatment temperature is generally higher than the decomposition temperature of the organic complex and the especially the partially decomposed organic complex.

If a plurality of active metals are to be applied to the support and the application is carried out in succession, the various process stages of the present invention may be repeated in order to deposit each metal in sequence.

The total metal surface area is ideally within the range from 0.01 to 30 m$^2$/g, preferably from 0.05 to 25 m$^2$/g, more preferably from 0.05 to 20 m$^2$/g, even more preferably from 0.05 to 15 m$^2$/g, more preferably from 0.05 to 10 m$^2$/g, even more preferably from 0.05 to 5 m$^2$/g and most preferably from 0.05 to 3 m$^2$/g of the catalyst. The metal surface area may be measured by the chemisorption method as herein described.

The catalysts obtained from the processes of the first, second, third and fourth aspects of the present invention and according to the fifth and sixth aspect of the present invention may be used in a wide variety of processes for the conversion or organic compounds where a chemical reaction occurs and is catalyzed. In addition the materials obtained from the first, second, third and fourth aspects of the present invention may be used in a wide variety of processes for the treatment of organic compounds or mixtures of organic compounds in order to convert or remove relatively small amounts of impurities; in this application the materials obtained from the processes of the present invention may be acting as adsorbents.

Of particular interest in the present invention is the production of C$_5$+ liquid hydrocarbons from a hydrogen and carbon monoxide synthesis gas by contact of the said gas at reaction conditions with a catalyst obtained from the processes according to the first, second, third and fourth aspects of the present invention or according to the fifth and sixth aspect of the present invention.

Of particular interest in the present invention is the treatment of organic compounds especially hydrocarbons in admixture with quantities of sulfur containing compounds especially organosulfur compounds, with materials obtained from the processes of the first, second, third and fourth aspects of the present invention or the catalyst of the fifth and six aspects of the present invention, in order to remove some or all of the sulfur from the organic compounds. Preferably this treatment is under the normal conditions for Sulfur Trim treatment and in the absence of hydrogen.

The process of the present invention is further illustrated by means of the following examples.

EXAMPLES

Example 1a

Preparation of MCM-41

A sample of MCM-41 (40 Å) was prepared in accordance with the method described below, which corresponds to Example 21 of U.S. Pat. No. 5,837,639. The following mixture (parts by weight—pbw) was charged to an autoclave:

83.7 pbw Cetyltrimethylammonium (CTMA) hydroxide prepared by contacting a 29 wt. % N,N,N-trimethyl-1-hexadecylammonium chloride solution with a hydroxide—for halide exchange resin, 1.7 pbw sodium aluminate, 41.1 pbw tetramethylammonium silicate (10% aqueous solution), and 10.5 pbw precipitated hydrated silica (HiSil)

The mixture was crystallized at 100° C. for 20 hours with stirring under autogeneous pressure. The resulting product was recovered by filtration and dried in air at ambient temperature. The product was then calcined at 540° C. for one hour in nitrogen, followed by six hours in air. The calcined product had a surface area of 1120 m$^2$/g and the following equilibrium adsorption capacities in gram/100 grams:

| | |
|---|---|
| H$_2$O | 10.8 |
| Cyclohexane | >50 |
| n-Hexane | >50 |
| Benzene | 67 |

The product was identified as MCM-41 with an X-ray diffraction pattern that included a very strong relative intensity line at 38.4+/−2.0 Å, and weak lines at 22.6+/−1.0, 20.0+/−1.0, and 15.2+/−Å.

Example 1b

Preparation of MCM-41

A sample of MCM-41 (40 Å) was prepared in accordance with the following method. The following mixture (parts by weight—pbw) was charged to an autoclave:

26.8 pbw distilled water, 3.5 pbw Cetyltrimethylammonium (CTMA) chloride (29 wt. % aqueous solution), 4.55 pbw precipitated hydrated silica (Ultrasil PM), 1 pbw Tetramethylammonium hydroxide (25 wt. % aqueous)

The mixture was crystallized at 150° C. for 20 hours with stirring under autogeneous pressure. The resulting product was recovered by filtration and dried in air at ambient temperature. The product was then calcined at 540° C. for one hour in nitrogen, followed by six hours in air. The product was identified as MCM-41. The calcined product has a surface area of 903 m$^2$/g and a pore size (determined by nitrogen adsorption) of 3.8 nm. The analyses are as follows:

| | |
|---|---|
| Silica | 96.8 wt. % |
| Alumina | 0.1018 wt. % |
| Sodium | 0.0300 wt. % |
| Carbon | 0.11 wt. % |

Sorption capacities were as follows:

| | |
|---|---|
| H$_2$O | 5.9 wt. % |
| Cyclohexane | 53.9 wt. % |
| n-Hexane | 44.1 wt. % |

Example 2

Preparation of Catalyst-Ruthenium and MCM-41-TEA/Aqueous Method

A solution was prepared by combining with stirring 16.6 grams of ruthenium (III) nitrosyl nitrate aqueous solution with 25.7 grams of triethanolamine and 25.7 grams of distilled water. This solution was added slowly to 25 grams of MCM-41 of Example 1b and dried overnight at 100° C. The catalyst was then calcined to 400° C. for three hours in flowing air. This resulted in complete decomposition of the organic complex. The ruthenium content was a nominal 0.5%.

Example 3

Preparation of Catalyst—Ruthenium and MCM-41 Aqueous Method

A solution was prepared by combining with stirring 16.6 grams of ruthenium (III) nitrosyl nitrate aqueous solution with 51.4 grams of distilled water. This solution was added slowly to 25 grams of MCM-41 of Example 1b and dried overnight at 100° C. The catalyst was then calcined to 400° C. for three hours in flowing air. This resulted in complete decomposition of the organic complex. The ruthenium content was a nominal 0.5%.

Example 4

Reduction of Metal Component of Hydrogenation Catalysts of Examples 2 and 3

The catalysts prepared in Examples 2 and 3 were activated under two sets of conditions a) and b) as follows:

a) Catalyst particles (10/20 mesh) were loaded into a stainless-steel catalyst basket then installed in a 300 cm$^3$ autoclave. Metal reduction was conducted under a continuous atmospheric hydrogen flow of ~100 cm$^3$ min$^{-1}$ at 200° C. for 18 hours.

b) Catalyst particles (10/20 mesh) were loaded into a stainless-steel catalyst basket then installed in a 300 cm$^3$ autoclave. Metal reduction was conducted under a static hydrogen pressure of 1250 psig at 200° C. for 14 hours.

Example 5

Hydrogen Treatment and Measurement of H Chemisorption Values for Supported Ru Catalysts of Examples 6 to 14

(A) Activation. Approximately 0.3 to 0.5 gram catalyst was loaded in the chemisorption cell, reduced in flowing hydrogen at one atmosphere total pressure at the temperature indicated in Tables 1 to 5. The samples were heated to the final reduction temperature at 2° C./min and held at this temperature for three hours. After this treatment the catalyst was activated and ready for use as a catalyst.

(B) The chemisorption measurements were obtained under static high vacuum conditions. After the hydrogen treatment under (A) hydrogen was then pumped off under dynamic vacuum for 15-30 minutes at the reduction temperature indicated in Tables 1 to 5. The temperature was lowered to 40° C. and an 8-point isotherm (with pressures between 80 and 400 torr) was obtained using H$_2$ as the chemisorption probe molecule. The linear portion of this isotherm was extrapolated to zero pressure to obtain the total quantity of hydrogen chemisorbed. This is shown in Tables 1 to 5 in the column labeled % dispersion (combined). The sample was evacuated at 40° C. to remove any weakly adsorbed hydrogen and the titration repeated to determine the weak adsorption isotherm. The linear portion of this isotherm was extrapolated to zero pressure to obtain the quantity of weakly chemisorbed hydrogen. This is shown in Tables 1 to 5 as the column labeled % dispersion (weak). Subtraction of these two values yields the strongly held chemisorbed quantity and is shown in accompanying tables below in the column labeled % dispersion (strong). All values are based on a H/Ru$_{surface}$ ratio of 1.

Example 6

Preparation of Organic Complex Comprising 0.5% Ru on SiO$_2$ Using Aminoalcohol in Impregnation Solution 15.00 g of silica support (S.A=85 m$^2$/g, P.D.=50 nm) was impregnated with solution prepared by mixing 5.01 g of ruthenium nitrosyl nitrate (1.5% Ru), 2.23 g triethanolamine and 1.77 g water and dried at 100° C. for four hours.

Example 7

Calcination of Catalyst of Example 6 to 300° C.

A portion of sample from Example 6 was calcined in flowing air as the temperature was ramped 1° C./minute to 300° C. and held for one hour at that temperature. This treatment resulted in the partial decomposition of the organic complex. A chemisorption measurement was made on this sample after hydrogen treatment.

Example 8

Calcination of Catalyst of Example 6 to 400° C.

A portion of sample from Example 6 was further calcined in air at a heating rate of 1° C./min to 400° C. and held at that temperature for 3 hours. This resulted in the complete decomposition of the organic complex. A chemisorption measurement was made on this sample after hydrogen treatment.

Table 1 compares the dispersion measurements by H chemisorption of the catalysts of Examples 7 and 8. This comparison shows that the highest dispersions are obtained when the Ru-TEA on silica catalyst is calcined at 300° C., which partially decomposes the complex. After 400° C. calcination the organic complex is totally destroyed before hydrogen treatment and it can be seen that the chemisorption values are substantially lower and are unstable as they decrease as the reduction temperature is increased above 250° C. The higher values in Example 7 catalyst remain stable during reduction at 400° C.

Example 9

Preparation of 0.5% Ru on $SiO_2$ Using Aminoalcohol in Impregnation Solution 25.00 g of silica support (S.A=250 $m^2$/g, P.D.=15 nm) was impregnated with solution prepared by mixing 8.37 g of ruthenium nitrosyl nitrate (1.5% Ru), 3.71 g triethanolamine and 18.00 g water and dried at 100° C. for four hours.

Example 10

Calcination of Catalyst of Example 9 to 275° C.

A portion of sample from Example 9 was calcined in flowing air as the temperature was ramped 1° C./minute to 275° C. and held at that temperature for one hour. This treatment resulted in the partial decomposition of the organic complex. A chemisorption measurement was made on this sample after hydrogen treatment.

Example 11

Pyrolyzing Catalyst of Example 9 in Oxygen-Free Environment

A portion of the sample from Example 9 was heated in flowing nitrogen as the temperature was ramped 2° C./minute to 400° C. and held at that temperature for one hour. This treatment resulted in the complete decomposition of the organic complex. A chemisorption measurement was made on this sample after hydrogen treatment.

Table 2 compares the dispersion measurements by H chemisorption of the catalysts of Examples 10 and 11. Both treatments generate a remnant of the starting Ru-triethanolamine complex. This comparison shows that the partial decomposition may be achieved at higher temperatures when under inert pyrolysis conditions (absence of oxygen) to form the Ru-organic precursor that gives high dispersion as well as when produced via oxidation.

Example 12

Sample of 0.5% Ru on Silica with no Organic Additive 15.00 g of silica support (S.A=85 $m^2$/g, P.D.=50 nm was impregnated with solution prepared by mixing 5.00 g of ruthenium nitrosyl nitrate (1.5% Ru) and 4.00 g water and dried at 100° C. for four hours. A chemisorption measurement was made on this sample after hydrogen treatment.

Example 13

Sample of 0.5% Ru on Silica with No Organic Additive and Calcination 15.00 g of silica support (S.A=85 $m^2$/g, P.D.=50 nm) was impregnated with solution prepared by mixing 5.00 g of ruthenium nitrosyl nitrate (1.5% Ru) and 4.00 g water and dried at 100° C. for four hours. The sample was then calcined in air as the temperature was ramped 1° C./minute to 300° C. and held at that temperature for one hour. A chemisorption measurement was made on this sample after hydrogen treatment.

Table 3 compares the dispersion measurements by H chemisorption of the catalysts of Examples 7, 12 and 13. Only the catalyst prepared according to Example 7 in the Table is an object of this invention and has the remnant of the starting Ru-triethanolamine complex. This comparison shows that a high initial dispersion can be obtained on a catalyst that is simply impregnated with an aqueous solution of the Ruthenium salt and then dried at low temperature if it is reduced at temperatures as low as 150° C. On reduction at higher temperatures the dispersion numbers decrease dramatically, most probably as a result of sintering. This does not happen with the catalyst of Example 7, which remains stable at 400° C. reduction temperatures. If the aqueous salt solution of Ru is calcined first to 300° C. the dispersion numbers are very low (Example 13).

Example 14

Preparation of 0.5% Ru on $SiO_2$ Using Aminoacid in Impregnation Solution 10.00 g of silica support (S.A=85 $m^2$/g, P.D.=50 nm) was impregnated with solution prepared by mixing 3.34 g of ruthenium nitrosyl nitrate (1.5% Ru), 0.70 g L-arginine, and enough water to form a total 10 cc solution volume. The sample was dried at 100° C. for four hours and the temperature was then ramped 1° C./minute to 250° C. and held at that temperature for one hour. A chemisorption measurement was made on this sample after hydrogen treatment.

Table 4 compares the dispersion measurements by H chemisorption of the catalysts of Examples 7 and 14. Both calcined samples leave a remnant of the starting Ru-amino complexes. This comparison shows that high dispersions are obtained when using either aminoalcohols or aminoacids in the impregnation solution.

The data Table 5 shows the chemisorption data for Examples 9 and 10. This comparison shows that the dried catalyst with the amino complex (Example 9) gives a good dispersion value if directly reduced in hydrogen that is superior to the sample where the complex is completely oxidized to remove the complex (Example 8 see Table 1). However, the dispersion is not as good as that obtained if the organic complex is either partially oxidized or pyrolyzed.

Example 16

Measurement of Decomposition Products of Catalyst Precursor Formed by Partial Oxidation of Ru-Triethanolamine Complex A portion of the catalyst from Example 7 was heated in air at 4 deg/min and the product gas was analyzed by a quadrupole mass spectrometer. The data is shown in FIG. 1. FIG. 1 shows that a water peak is released slightly below 200° C. and then there is formation of $CO_2$, $NO_2$ and $H_2O$ as the organic complex is completely oxidized near to 350° C. This shows that the complex contained C, N and H. There may also be 0 present but this could not be determined using this experiment as the conditions used were oxidizing conditions.

Example 17

Infra-Red Spectroscopy

The samples containing partially decomposed organic complex derived from Ru-triethanolamine and Ru-arginine were also analyzed using infrared spectroscopy. Approximately 25 mg of the materials of Example 7, (TEA, calc 300° C.), Example 12 (no organic, dry 100° C.) and Example 14 (L-arginine, calc 250 C) were separately formed into 13 mm pellets and loaded into an IR spectrometer operating in transmission mode. The samples were heated in vacuum to 150° C. before the spectra were obtained.

Figure 2:
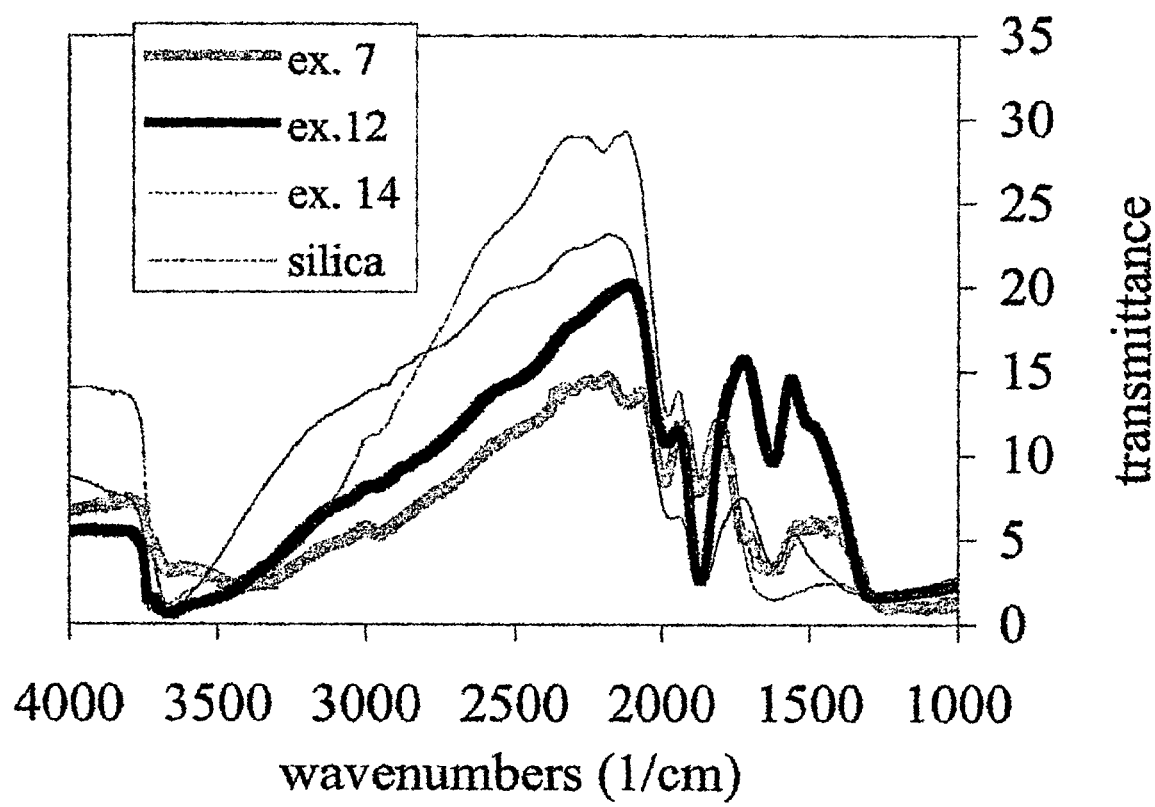
FIG. 2 shows the transmission infra-red spectra of silica and Examples 7, 9 and 14.

The data are shown in FIG. 2. The data shows the plot of transmittance vs. wave number of the IR radiation. The transmittance decreases where the catalyst absorbs infrared radiation due to a characteristic stretching of a molecular species. The peaks between 1500 and 2000 $cm^{-1}$ are primarily silica stretching bands. The presence of absorption features around 2100-2200 $cm^{-1}$, present on samples from Examples 7 and 14 are reported to be features of complexed carbon nitrogen species such as nitrites and isonitriles (see: Infrared and Raman Spectra of Inorganic and Coordination Compounds, by K. Nakamoto, John Wiley publishers, 3rd edition, 1978; ISBN: 0-471-62979-0, pages 267-269). The peaks are absent on the starting silica as well as on the sample prepared by aqueous impregnation of the ruthenium complex with no amino alcohol or amino acids present. Consequently these peaks are an indication of the remnant of the starting Ru-triethanolamine and Ru-arginine complexes present after partial decomposition of the organic complex.

Example 18

Thermogravimetric Analysis

Figure 3:
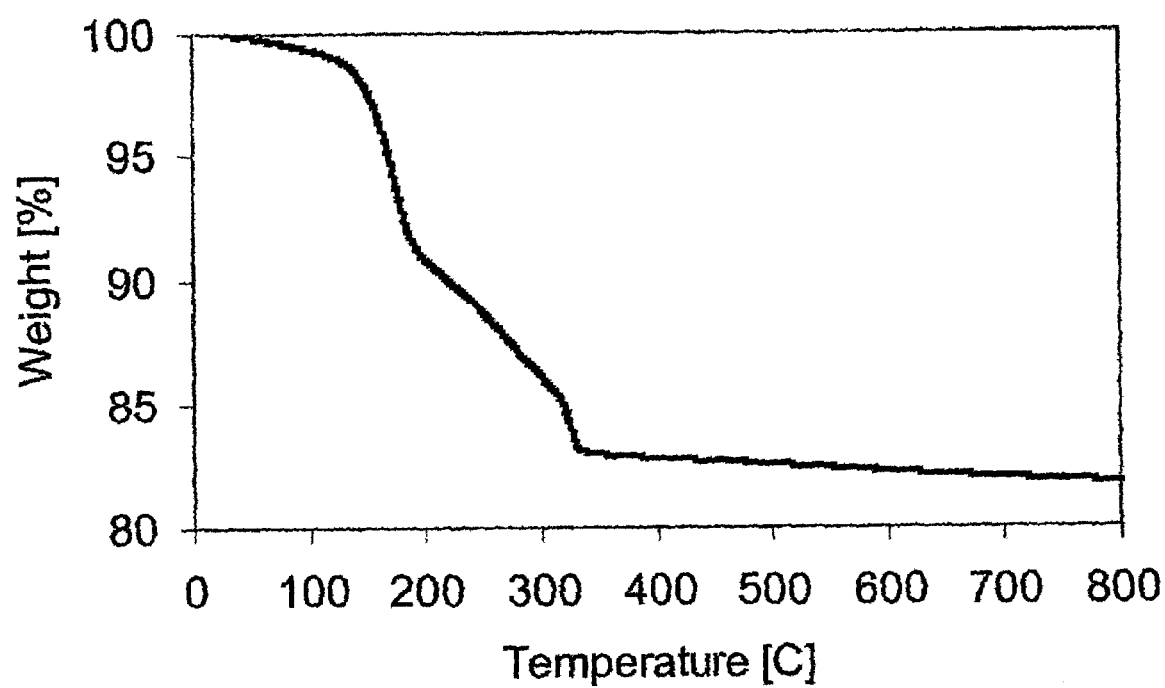
FIG. 3 shows an air treatment TGA plot for a supported metal catalyst (0.5 wt % Ru/SiO$_2$) prepared using impregnation of the metal with triethanolamine and drying at 100° C.

FIG. 3 shows the air treatment TGA plot for a catalyst sample (0.5 wt % Ru on $SiO_2$), which had been prepared with triethanolamine as the organic compound and dried at 100° C. prior to analysis. The TGA plot shows weight loss at temperatures below 300° C. due to loss of water and partial oxidation of the complex with triethanolamine. In addition there is a further weight loss at approximately 325° C., which is believed to be due to the complete oxidation of the organic complex.

Figure 4:
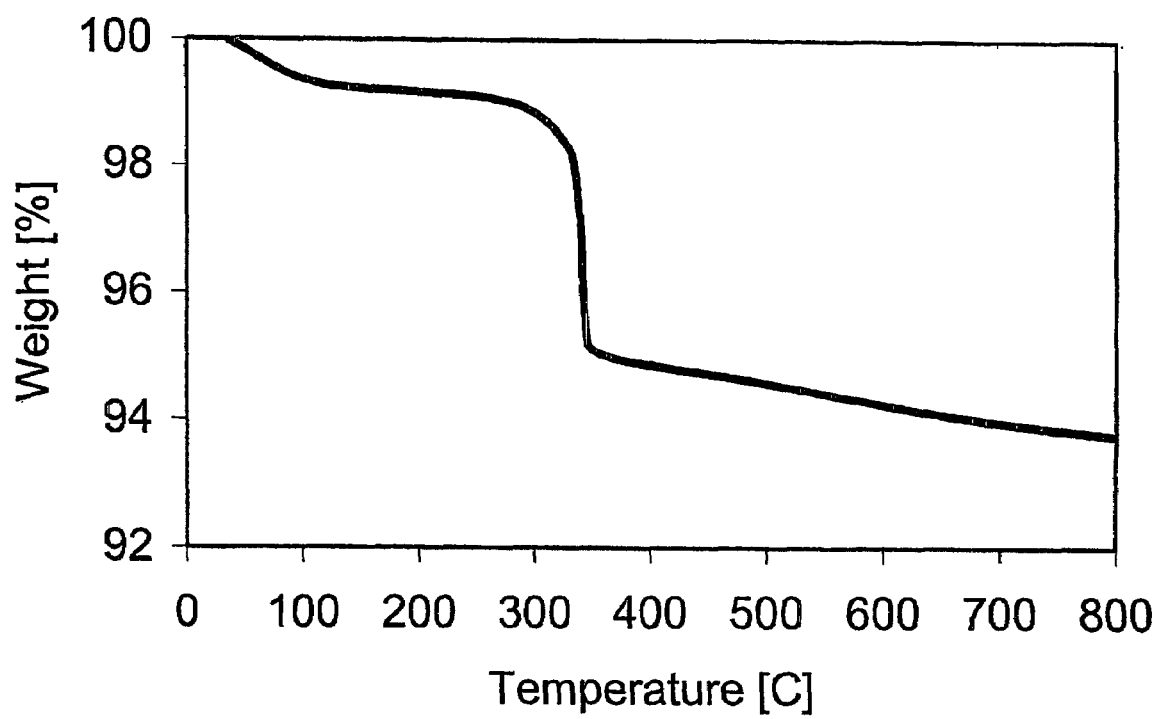
FIG. 4 shows an air treatment TGA plot for a supported metal catalyst (0.5 wt % Ru/SiO$_2$) prepared using impregnation of the metal with triethanolamine and calcination at 300° C.

FIG. 4 shows the air treatment TGA plot for a similar catalyst to that used in FIG. 1 (0.5 wt % Ru on $SiO_2$), which had previously been calcined at 300° C. Clearly there is an insignificant weight loss below 300° C.; this is due to the fact that any material on the supported catalyst that would have been removed below this temperature has been removed by the calcination. The majority of the weight loss in the sample is due to the partially decomposed organic complex, which is oxidized at approximately 325° C. This results shows that that calcination below the decomposition temperature is necessary to form the partially decomposed organic complex.

Figure 5:
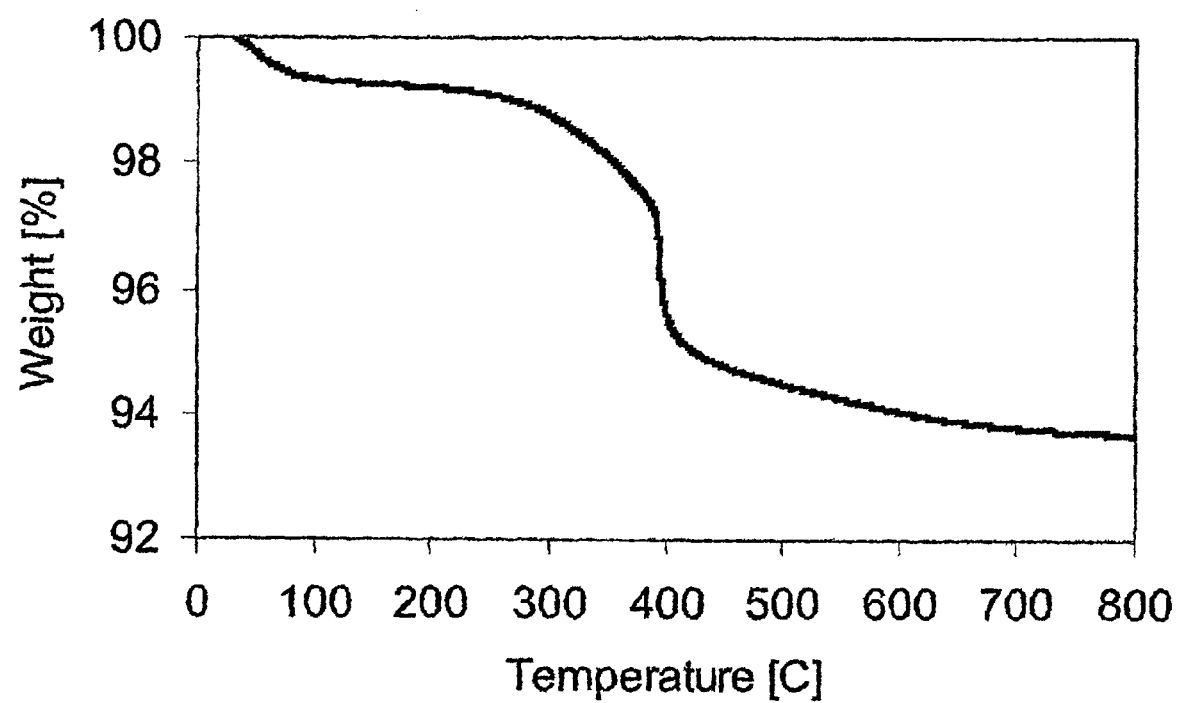
FIG. 5 shows a hydrogen treatment TGA plot for a supported metal catalyst (0.5 wt % Ru/SiO$_2$) prepared using impregnation of the metal with triethanolamine and calcination at 300° C.

FIG. 5 shows the hydrogen treatment TGA for the catalyst sample (0.5 wt % Ru on $SiO_2$), which had previously been calcined at 300° C. This TGA analysis shows that the partially oxidised organic complex is fully decomposed under the hydrogen treatment conditions at a higher temperature (~400° C.) than under calcination conditions.

Example 19

Preparation of 3% $ZrO_2/TiO_2$ (Anatase) Support

A support consisting of >80% anatase, and with a surface area of 48 $m^2/g$ was first slurried in a solution kept at pH 11 by addition of $NH_4OH$. The suspension was kept stirring for one hour at 60-70° C. The solid was then filtered and washed with a 1M solution of $NH_4OH$ to remove any excess chloride until the filtrate, when added to a silver nitrate solution did not produce a white precipitate. Onto 20 grams sample of this titania support, 12 cc of aqueous solution containing 1.52 g of $ZrO(NO_3)_2 \cdot 4H_2O$ was impregnated to the incipient wetness point and dried overnight at 120° C. The sample was then calcined at 450° C. to form a 3% $ZrO_2/TiO_2$ support. This procedure was repeated 10 times and all the samples mixed together.

Example 20

Preparation of a (Nominal) 11% Co-1% Re on 3% $ZrO_2/TiO_2$ (Anatase) Support 12.3 g of cobalt nitrate hexahydrate and 0.35 grams of a solution of perrhenic acid containing 65% Re were dissolved in an aqueous solution of 7 cc total volume to form an impregnation solution. The impregnation solution was then heated to 40° C. prior to impregnation to facilitate dissolution of the cobalt nitrate. 20 grams of the support described in Example 19 was heated to ~60° C. and impregnated with the impregnation solution. The impregnation was carried out by incipient wetness. The sample was dried at 120° C. overnight. The composition as well as the metal content on catalysts in this Example and Examples 21 to 29 was based on the calculated amount of metals in the reduced catalyst.

Example 21

Preparation of a Nominal 11% Co-1% Re on 3% $ZrO_2/TiO_2$ (Anatase) Catalyst (No Additive in Solution or Post-Treatment)

The impregnated material of Example 20 was calcined at 350° C. in air for 4 hours.

Example 22

Preparation of 11% Co-1% Re on 3% $ZrO_2/TiO_2$ (Anatase) with DMEA Post-Treat on Dried Impregnate Sufficient water was added to 3.8 grams of N,N-dimethylethanolamine to make a solution of 7 cc. This solution was impregnated by incipient wetness onto 20 grams of the 120° C.-dried, impregnated material of Example 20. The sample was dried at 120° C. overnight and then calcined at 350° C. for four hours. This resulted in the complete destruction of the organic complex

Example 23

Preparation of 11% Co-1% Re on 3% $ZrO_2/TiO_2$ (Anatase) with DMEA Post-Treat on Calcined Impregnate Sufficient water was added to 0.4 grams of N,N-dimethylethanolamine to make a solution of 0.7 cc This solution was impregnated by incipient wetness onto the a two gram sample of the impregnated and 350° C.-calcined sample of Example 21. The sample was dried at 120° C. and then calcined at 350° C. for four hours. This treatment resulted in complete decomposition of the organic complex.

Example 24

Preparation of a Nominal 11% Co, 0.15% Re on TiO$_2$ Rutile with MDEA Posttreat on Dried Impregnate 20 g of a support consisting of >80% rutile, and with a surface area of 16 m$^2$/g, was impregnated by incipient wetness with 8 cc of an aqueous solution containing 12.3 g of cobalt nitrate hexahydrate and 0.052 grams of a solution of perrhenic acid (65% Re). The impregnation solution was heated to 40° C. and the support to ~60° C. prior to impregnation to facilitate dissolution of the cobalt nitrate. The impregnation was carried out by incipient wetness. The impregnated sample was dried at 120° C. for four hours. Sufficient water was added to 2.53 grams of N,N methyldiethanolamine to make a solution of 4 cc. This solution was then impregnated by incipient wetness onto 10 grams of the previously dried impregnate. This sample was dried at 120° C. and calcined at 350° C. and held at that temperature 4 hours (analysis 9.85% Co). This resulted in the complete decomposition of the organic complex.

Example 25

Preparation of 1% ZrO$_2$/TiO$_2$ Rutile

Onto 20 g of a support consisting of >80% rutile and with a surface area of 16 m$^2$/g a solution of 8 cc volume containing 0.497 grams of ZrO(NO$_3$)$_2$.4H$_2$O was impregnated by incipient wetness. This sample was then dried at 120° C. overnight and calcined at 450° C. for four hours.

Example 26

Preparation of a Nominal 11% Co, 0.15% Re on 1% ZrO$_2$/TiO$_2$ Rutile with TEA in the Solution Onto 20 g of a support consisting of >80% rutile with a surface area of 16 m$^2$/g, was impregnated as solution of 8 cc volume containing 0.497 grams of ZrO(NO$_3$)$_2$.4H$_2$O by incipient wetness. This sample was then dried at 120° C. overnight and calcined at 450° C. for four hours. Onto 20 grams of this sample was impregnated, a solution of 8 cc volume containing 12.25 g of cobalt nitrate hexahydrate, 0.052 grams of a solution of perrhenic acid (65% Re) and 3.13 grams of triethanolamine. The solution was heated to 40° C. and the support to ~60° C. prior to impregnation to facilitate dissolution of the cobalt nitrate. The impregnation was carried out by incipient wetness. This sample was dried at 120° C. overnight and then heated to 350° C. in air at 1 deg/min and held at this temperature for 4 hours. (Chemical analysis 0.13% Re, 9.57% Co). This resulted in the complete decomposition of the organic complex.

Example 27

Preparation of a Nominal 10.6% Co, 0.7%% Re on 1% ZrO$_2$/TiO$_2$ Rutile (No Additive in Solution or Post-Treatment)

10 g of a 1% ZrO$_2$/TiO$_2$ (rutile) support prepared as described in Example 25 was chosen. A solution containing 5.92 g of cobalt nitrate hexahydrate and 0.114 grams of a solution of perrhenic acid (65% Re) was prepared and heated to 40° C. to facilitate dissolution of the cobalt nitrate. The support was heated to ~60° C. prior to impregnation with the solution and the impregnation was carried out by incipient wetness. This sample was dried at 120° C. overnight and then heated to 350 C in air at 1 deg/min and held at this temperature for 4 hours. (Chemical analysis: 9.3% Co, 0.6% Re).

Example 28

Preparation of 11.3% Co, 0.9% Re on TiO$_2$ Rutile (no Additive in Solution or Post-Treatment)

A sample similar to that described in Example 27 was prepared on the rutile support which did not have any additional Zr added to it. The sample analyzed as 11.3% Co and 0.9% Re.

Example 29

Preparation of 9.2% Co, 1.2% Re on SiO$_2$ with TEA in Solution 70.01 g of silica support (S.A=50 m2/g) was impregnated with a solution prepared by mixing 46.27 g of cobalt nitrate hexahydrate, 11.46 g water and 11.85 g triethanolamine and dried at 60 C for two hours. After the initial two hours drying the oven temperature was increased to 70° C. and held for 1 hour. The drying temperature was increased to 80° C., 100° C. and 140° C. with one-hour intervals at each temperature. Upon completion of this procedure the sample color changed form pink to black. The dried sample was calcined in flowing air by gradually ramping the temperature in the following protocol to temper the vigorous oxidation reaction between cobalt nitrate and the aminoalcohol: 2° C./minute to 145° C. and hold for one hour, 2° C./minute to 180° C. and hold for one hour, 2° C./minute to 200° C. and hold for one hour, 2° C./minute to 300° C. and hold for one hour. This resulted in the complete decomposition of the organic complex.

Example 30

Preparation of 9.9% Co-1.3% Re on SiO$_2$ with No Additive in Solution 15.01 grams of a silica support (43 m$^2$/g) was impregnated to the incipient wetness point with 8.7 ml of solution prepared by dissolving 8.28 grams cobalt nitrate hexahydrate and 0.41 grams perrhenic acid solution (54% Re) in 3.99 grams water. The sample was then dried at 60° C. in air and calcined at 300° C. in air for 1 hr.

Example 31

Hydrogen Treatment and Chemisorption Procedure for the Catalysts of Examples 21-30

Strong metal-support interactions are known to affect the performance of the particle/support system in many applications. The support materials can interact with the active metal; such interactions of the metals with reducible oxides resulting from high reduction temperatures (over 700 K) are generally referred to as "Strong Metal-Supported Interactions" (SMSI). In many instances SMSI is detrimental to the catalyst activity and performance. SMSI causes the partially reduced support to partially cover metal particles deposited on the support blocking their active surface sites. For further information on SMSI reference should be made to "Strong Metal Support Interactions. Group 8 Noble Metals Supported on Titanium Dioxide", Tauster, S. J.; Fung, S. C.; Garten, R. L, Journal of the American Chemical Society, (1978), 100(1), 170-5.

In an attempt to minimize SMSI effecting the chemisorption measurements, $TiO_2$-supported catalysts in Examples 21-23 were ex-situ high temperature reduced [450° C.], passivated and partially reoxidized [at 150° C.]. These samples were then subjected to hydrogen treatment for a final reduction in the chemisorption instrument at the low temperature of 225° C. and in the presence of hydrogen before their chemisorption properties were measured. The catalysts of Examples 29 and 30, which are supported on silica and as such do not exhibit SMSI, were reduced in the chemisorption apparatus at 2° C. per minute to 450° C. for 90 mins in the presence of hydrogen. In all cases approximately 0.3-0.5 grams of catalyst was reduced under one atmosphere hydrogen.

Chemisorption measurements were obtained under static high vacuum conditions on a Quantachrome Autosorb 1A instrument. For determination of dispersion all the samples were loaded into a chemisorption unit and the reduction was undertaken in this unit. After reduction the hydrogen was pumped off under dynamic vacuum for 45 minutes at the reduction temperature, the temperature was lowered to 40° C. and an 8 point isotherm (with pressures between 80 and 400 torr) was obtained. $H_2$ was used at the chemisorption probe molecule. The sample was evacuated at the chemisorption temperature to remove any weakly adsorbed hydrogen and the titration repeated to determine the weak adsorption isotherm. Subtraction of the two isotherms yields the strongly chemisorbed isotherm and its extrapolated intercept at 0 torr corresponds to monolayer gas coverage. This value was used to estimate cobalt dispersions (based on a H/Co surface ratio of 1). The reductions for Examples 21-23 were then repeated at the same [225° C.] reduction temperature [for 180 minute intervals] to make certain that all the Co that will reduce at the given temperature has actually reduced.

Since hydrogen chemisorption on the silica supported catalysts does not require breaking the SMSI state, the catalysts of examples 29 and 30 were directly reduced in the chemisorption apparatus as indicated above. These samples were then evacuated at the reduction temperature and the combined and weak hydrogen adsorption isotherms were measured at 40° C. Successive reduction cycles [for 180 minutes] check that additional cobalt was not being reduced.

In Table 6 the chemisorption values for the Co, Re catalysts of examples 20-22 are indicated along with particle size values determined by transmission electron microscopy. Where any additional reduction has occurred following the initial reduction cycles, the maximum chemisorption values are chosen. Those skilled in the art recognize that Re addition to supported Co catalysts lowers reduction temperature and decreases particle size (i.e. increases dispersion). Examples 21, 22 and 23 suggest that for the aminoalcohol post-treated samples on a ZrO2 modified anatase support, at the same Re level, there was an improved dispersion, with the better result occurring on the dried (Example 22) rather than calcined impregnate (Example 23). Examples 24-27 show that the aminoalcohol addition or post-treatment allows the attainment of the same dispersion as increasing Re levels by a factor of 3 to 5 on rutile type supports. Examples 29 and 30 show a dramatic improvement on silica catalysts for impregnations undertaken using the process of the present invention.

Example 32

TEM Analysis

Figure 6:
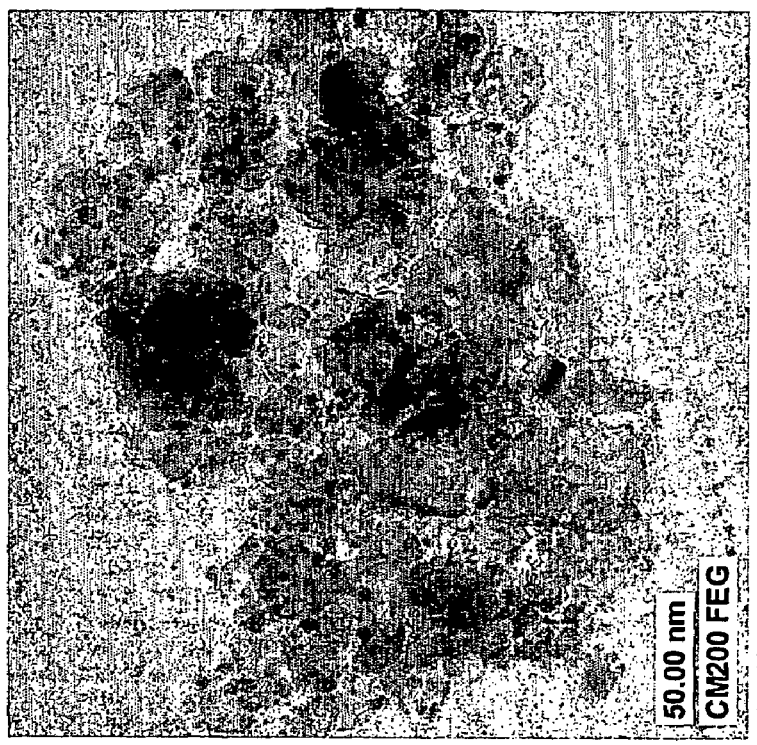
FIG. 6(a) shows a TEM micrograph of the catalyst of Example 21 showing the Co particles on the ZrO2/TiO2 (anatase support), after calcination at 350° C. and reduction.
FIG. 6(b) shows a TEM micrograph of the catalyst of Example 22 showing Co particles on the ZrO$_2$/TiO$_2$ (anatase support) after post-treatment of the dried impregnate with dimethylethanolamine, 350° C. calcination and reduction.
Figure 6:
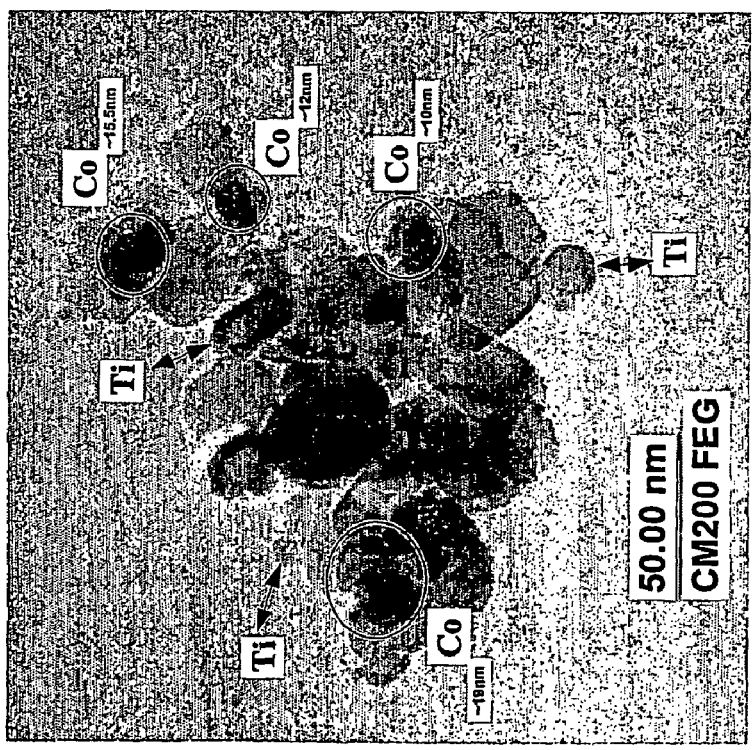

TEM micrographs of the catalysts of Examples 21 and 22 are compared in FIGS. 6(a) and 6(b) respectively. In FIG. 6(a) the micrograph of catalyst of Example 21 shows the Co particles on the ZrO2/TiO2 (anatase support). The catalyst was prepared by standard impregnation with no post-treatment nor any additions of dispersion aids to the impregnating solution. The catalyst was then calcined and reduced and inertly transferred into the TEM. Due to the similar size of the Co and support particles, in order to locate the Co particles among the anatase support particles, it was necessary to focus the TEM beam down to a small probe, ~10 nm in diameter. The probe was positioned on randomly selected particles within the image and energy dispersive spectroscopy (EDS) data was collected from each particle. The characteristic x-ray peaks in the EDS spectra were then identified as either Co or Ti (anatase). The Co particles identified in this image ranged from ~10 nm to ~19 nm in diameter. In FIG. 6(b) the TEM micrograph of the catalyst of Example 22 shows the Co particles on the $ZrO_2/TiO_2$ (anatase support) following post-treatment of the dried impregnate with dimethylethanolamine, calcination, reduction and inert transfer into the TEM. In this case, there was excellent contrast between the Co and support particles because of the large difference in their relative sizes. Note that Re levels in both catalysts are the same. Those skilled in the art recognize that Re addition to supported Co catalysts lowers reduction temperature and decreases particle size (i.e increases dispersion). In both cases the samples were reduced at 450° C. for 4 hours and then inertly transferred into the microscope without any intervening air exposure. The TEM data shows that post-treat of the dried Co, Re impregnate with DMEA increases the dispersion dramatically (i.e. the cobalt particles are much smaller (typically ~5 nm) and there is a more uniform nanoscale distribution of the cobalt in the catalyst.

Figure 10:
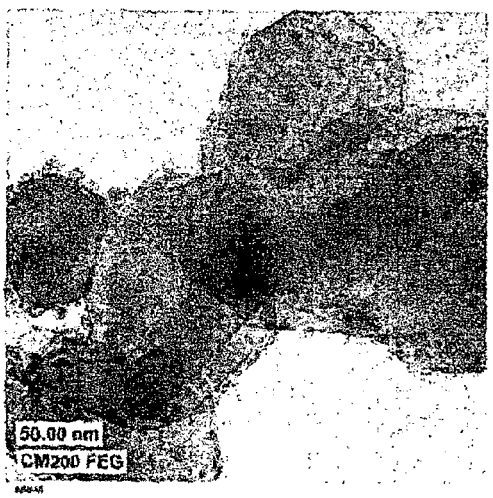
FIG. 10 shows the shows a TEM micrograph of the catalyst of Example 24 showing the Co particles on the support along with a histogram showing the particle size distribution for the Co metal on the support.
Figure 10:
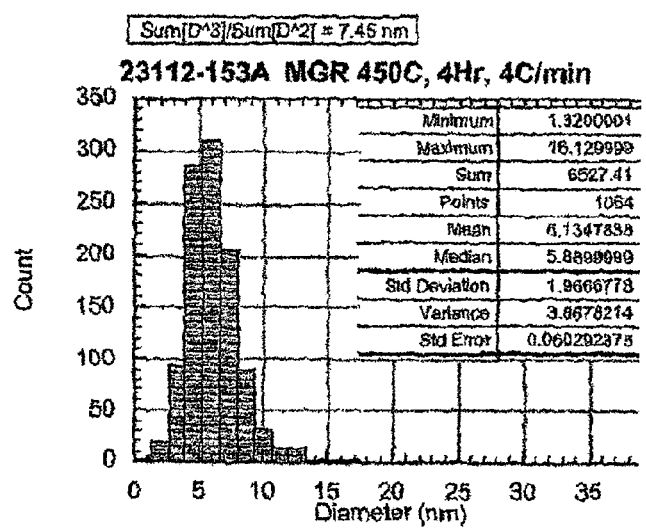

The TEM micrographs of the catalysts of Examples 24 is provided in FIG. 10 along with a histogram showing the particle size distribution for the Co metal on the support. The TEM shows remarkably even distribution of the Co metal particles on the support and the histogram shows that these particles have a mean particle size of approximately 6 nm with a maxim particle size of approximately 16 nm.

Example 33

SIMS Analysis

Figure 7:
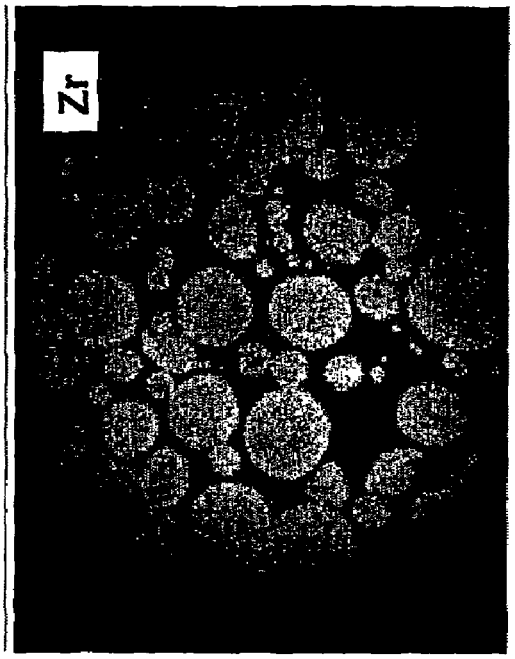
FIG. 7 shows the results of a SIMS analysis of the catalyst of Example 22, illustrating the location of Co, Ti and Zr.
Figure 7:
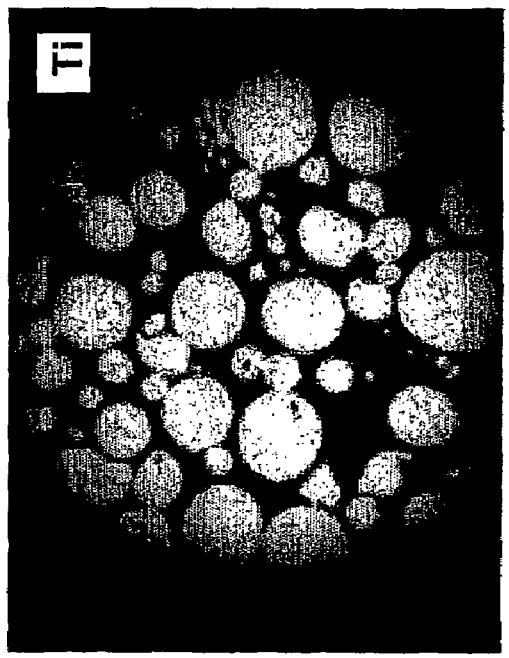
Figure 7:
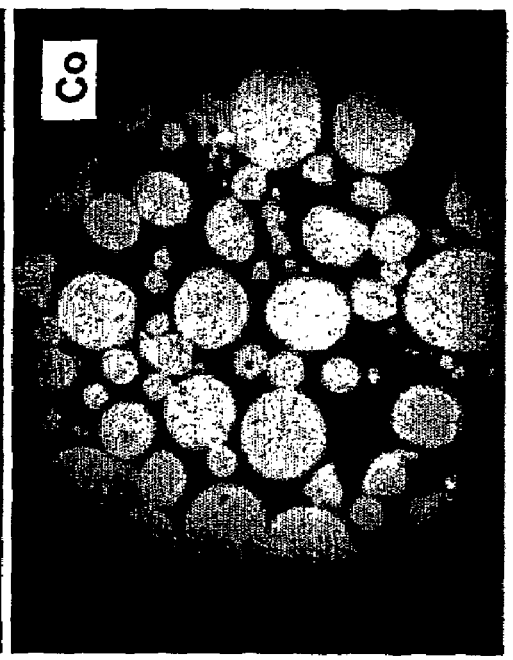
Figure 8:
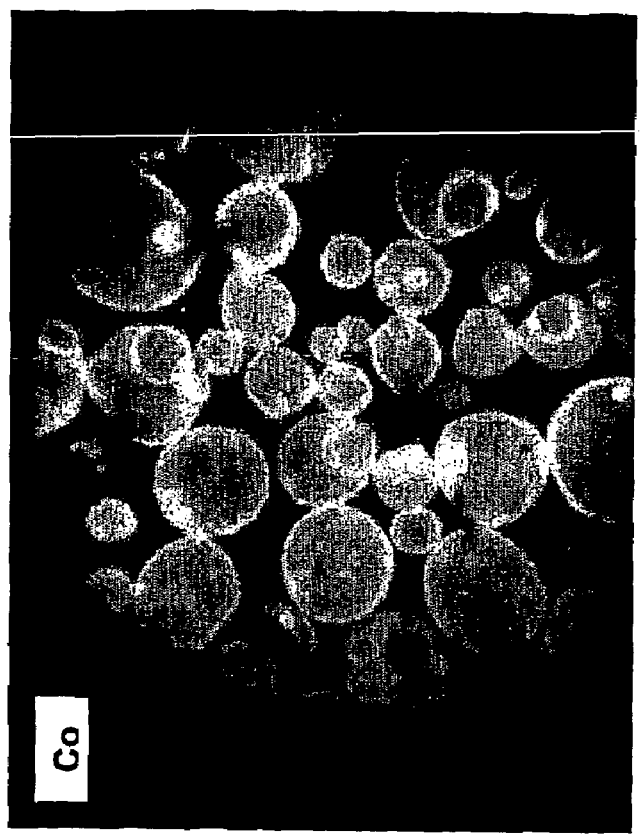
FIG. 8 shows the results of a SIMS analysis of the catalyst of Example 28, illustrating the location of Co and Ti.
Figure 8:
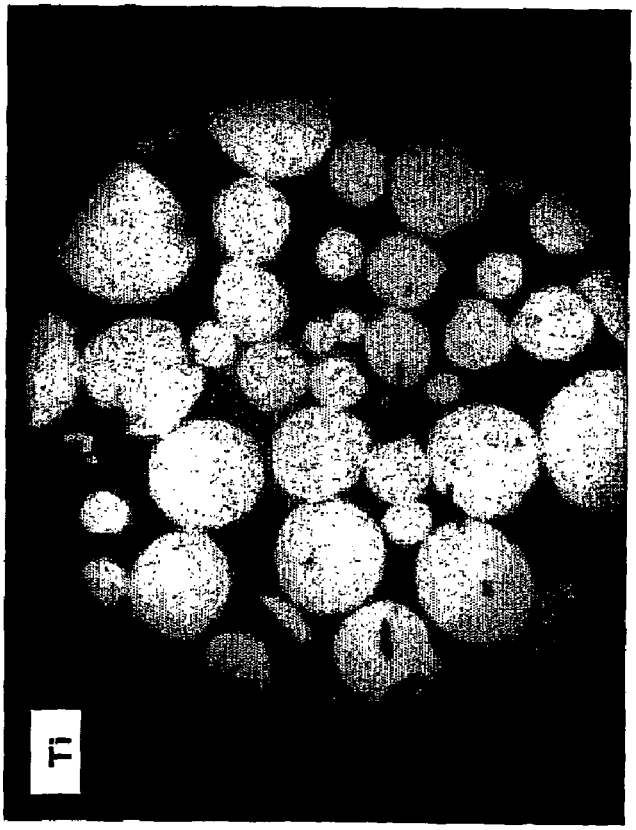

The catalysts of Examples 22 and 28 were evaluated by SIMS and the results are shown in FIGS. 7 and 8 respectively. The catalyst of Example 22 is seen to be a 30-40 micron agglomerated particle consisting of smaller particles grouped together. In the smaller particles one can see a very uniform distribution of cobalt with only minor visual brightness differences. In contrast the catalyst of Example 28, which is not prepared according to the present invention, shows the Co concentrated on the outside of the support. This comparison shows that through utilization of the process of the present invention at both the nano and microscale homogeneity in respect of Co dispersion is improved.

Example 34

Catalyst Testing: Fischer-Tropsch

Catalyst tests were performed in a down-flow fixed bed reactor. The 0.5" OD/0.43" ID stainless steel reactor body had a 0.125" OD thermocouple-well in the center. The thermocouple-well housed eight thermocouples 1.5" apart. The eight thermocouples of the reactor were calibrated and certified by the vendor. The volume of the catalyst plus diluent bed positioned between the top and bottom thermocouples was 23 mL. The reactor vessel was sleeved in a 2.5" diameter aluminum or brass cylindrical block to provide better heat distribution. Feed gas was fed to the catalyst bed through a 0.125" pre-heat tube housed in the brass or aluminum block to the feed introduction point at the top of the reactor. The reactor was heated by an infrared furnace and by a resistive auxiliary heater installed at the bottom of the brass (or aluminum) block. The latter was installed to ensure isothermal bed conditions. The catalyst bed was held in place by stainless steel filter discs both on the bottom and the top. In order to reduce the temperature spread in the catalyst bed during kinetic experiments, the catalyst was diluted with similarly sized quartz sand at a quartz-to-catalyst volume ratio of approx. 8:1. The axial temperature-spread in the catalyst bed at Fischer-Tropsch condition was typically 3 to 10 K. The average temperature of the catalyst bed was calculated as a weighted average. The weighting factor for the first and last thermocouple zones (entrance and exit points) was set to one-half of that of the internal thermocouple zones. Feed components were individually fed through Brooks mass-flow controllers and were purified before use.

Figure 9:
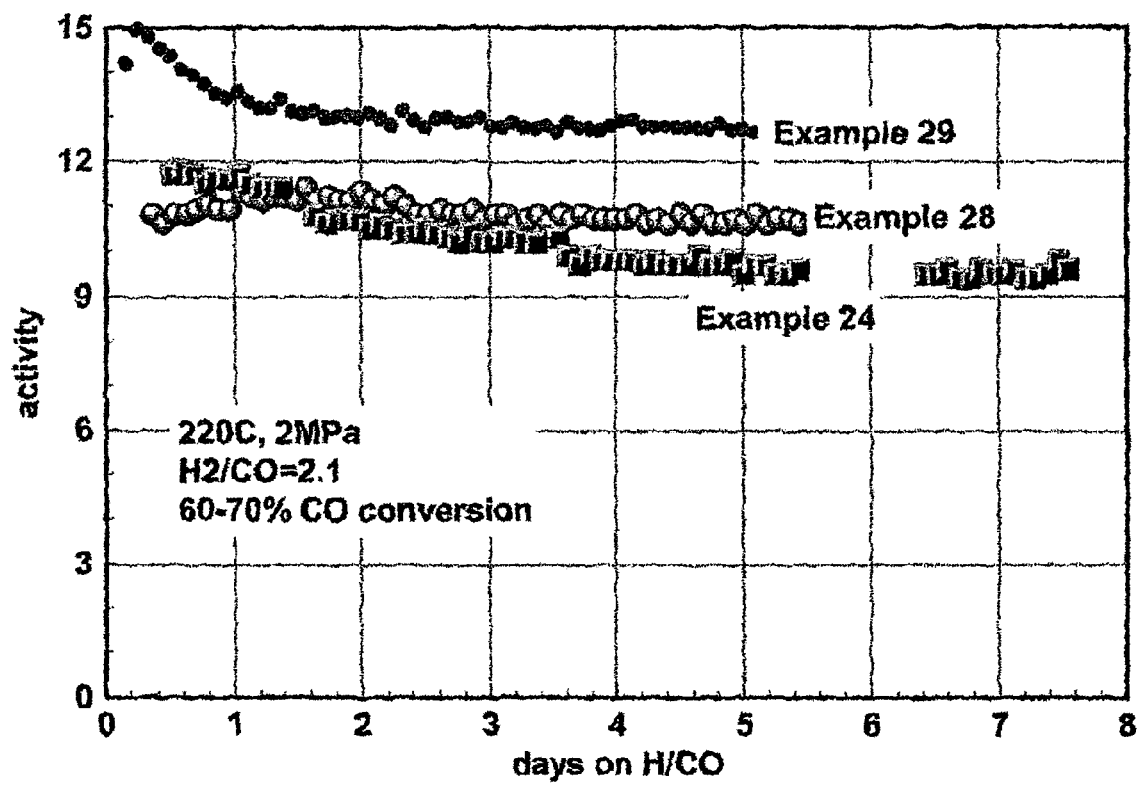
FIG. 9 shows the catalytic activity in CO conversion for the catalysts of Example 28 (11% Co, 1% Re/TiO$_2$ (rutile)), Example 24 (11% Co, 0.15% Re/TiO$_2$ (rutile), with MDEA post-treatment) and Example 29 (9.9% Co-1.3% Re on SiO$_2$ with TEA in solution)

In a typical fixed bed experiment, approximately 3 g of catalyst was diluted with quartz to 23 mL volume and charged into the reactor. The catalyst then was reduced in a flow of $H_2$ (450 standard mL/min) at 1.2 MPa by raising the temperature to 400° C. at a rate of 1° C./min and holding the final temperature for 8 hrs. The catalyst was then cooled to 160° C. in flowing $H_2$, put under 2 MPa of synthesis gas ($H_2/CO \approx 2.1$) pressure and, finally, brought up to synthesis temperature (220° C.) at a 1° C./min ramp rate. CO conversion was adjusted by changing the feed flow, which later is commonly expressed in Gas Hourly Space Velocity, or GHSV. GHSV is defined as standard volume of gas (at 70 F, 1 atm) feed per volume of catalyst per hour. During all tests CO conversion was maintained at a similar level (between 50 and 80%). FIG. 9 shows the initial catalytic activity of the base-case (conventional catalyst) and two catalysts, one on $TiO_2$ and the other on $SiO_2$ support, prepared according to the present invention. In FIG. 9 the initial catalytic activity of base-case—Example 28 (11% Co, 1% Re/$TiO_2$ (rutile), with no aminoalcohol treatment), Example 24 (11% Co, 0.15% Re/$TiO_2$ (rutile), MDEA post-treatment) and Example 29 (9.9% Co-1.3% Re on $SiO_2$ with TEA in solution). The data in FIG. 9 clearly demonstrates that high activity stable Fischer-Tropsch catalysts can be made using the process of the present invention. Example 24 has only 15% of the rhenium of Example 28 the base case but has comparable performance under FT conditions. Example 29 is significantly superior to the base case in performance under FT conditions.

Example 35

Preparation of 20% Ni/$Al_2O_3$ Conventional Preparation 20 grams of reforming grade gamma $Al_2O_3$ with a surface area of 190 m 2/g, was impregnated by incipient wetness with 12 cc of an aqueous impregnation solution containing 24.8 g of nickel nitrate hexahydrate. After being dried at 120° C., the sample was calcined at 350° C. for four hours.

Example 36

Preparation of 20% Ni/$Al_2O_3$ with DMEA Post-Treat on Dried Impregnate 20 grams of reforming grade gamma $Al_2O_3$ with a surface area of 190 m 2/g, was impregnated by incipient wetness with 12 cc of an aqueous impregnation solution containing 24.8 g of nickel nitrate hexahydrate. After being dried at 120° C., the sample was re-impregnated to incipient wetness with a 10.6 cc of an aqueous solution containing 7.6 grams of N,N-dimethylethanolamine. The sample was then dried at 120° C. overnight and then calcined at 350° C. for 4 hours. Under these conditions the organic complex was fully decomposed The dispersions of Ni the catalysts of Examples 35 and 36 was determined via a hydrogen chemisorption technique. The results are provided in Table 7. These results show a dramatic increase in Ni dispersion when the NI is deposited using the process of the present invention.

TABLE 7

| Sample | Treatment | Hydrogen chemisorption H/Ni in % |
|---|---|---|
| Ni/$Al_2O_3$ | | |
| Example 35 | No post-treat nor additions to impregnation solution | 8.3 |
| Example 36 | N,N dimethylethanolamine post-treat dried impregnate/oxidize | 11.6 |

Example 37

Preparation of 19.0% Ni on $SiO_2$ with No Additive in the Solution 15.02 grams of a silica support (80 $m^2$/g) was impregnated to the incipient wetness point with solution prepared by dissolving 17.49 grams nickel nitrate hexahydrate in 7.75 grams water. The sample was then dried at 120° C. in air and calcined at 350° C. in flowing air for 2 hr.

Example 38

Preparation of 18.0% Ni on $SiO_2$ with Tea Additive in the Solution, Molar Ratio of Tea/Ni=0.125

10.00 grams of a silica support (80 $m^2$/g) was impregnated to the incipient wetness point with solution prepared by dissolving 10.97 grams nickel nitrate hexahydrate in 4.52 grams water and 0.70 grams triethanolamine. The sample was then dried in air at 60° C. for and hour and at 90° C. for and hour. The dried sample was calcined in flowing air by gradually ramping the temperature in the following protocol to temper the vigorous oxidation reaction between nickel nitrate and the aminoalcohol: 2° C./minute to 195° C. and hold for one hour, 1° C./minute to 350° C. and hold for one hour. This treatment resulted in the complete destruction of the organic complex.

Example 39

Preparation of 18.0% Ni on $SiO_2$ with Tea Additive in the Solution, Molar Ratio of Tea/Ni=0.25

10.02 grams of a silica support (80 m²/g) was impregnated to the incipient wetness point with solution prepared by dissolving 10.93 grams nickel nitrate hexahydrate in 3.87 grams water and 1.40 grams triethanolamine. The sample was then dried in air at 60° C. for and hour and at 90° C. for and hour. The dried sample was calcined in flowing air by gradually ramping the temperature in the following protocol to temper the vigorous oxidation reaction between nickel nitrate and the aminoalcohol: 2° C./minute to 195° C. and hold for one hour, 1° C./minute to 350° C. and hold for one hour. This treatment resulted in the complete destruction of the organic complex.

Example 40

Preparation of 18.3% Ni on $SiO_2$ with Tea Additive in the Solution, Molar Ratio of Tea/Ni=0.50

15.02 grams of a silica support (80 m²/g) was impregnated to the incipient wetness point with solution prepared by dissolving 16.66 grams nickel nitrate hexahydrate in 4.01 grams water and 4.28 grams triethanolamine. The sample was then dried in air at 60° C. for and hour and at 90° C. for and hour. The dried sample was calcined in flowing air by gradually ramping the temperature in the following protocol to temper the vigorous oxidation reaction between nickel nitrate and the aminoalcohol: 2° C./minute to 165° C. and hold for one hour, 1° C./minute to 350° C. and hold for one hour. This treatment resulted in the complete destruction of the organic complex.

Example 41

Hydrogen Treatment and Chemisorption Procedure for Examples 37 to 40

Prior to chemisorption measurements the samples were reduced under 1 atmosphere hydrogen at a temperature of 450° C. for 90 minutes. Chemisorption measurements were obtained under static high vacuum conditions on a Quantachrome Autosorb 1A instrument. The catalysts are loaded into the chemisorption unit. Approximately 0.3-0.5 grams of catalyst are reduced under one atmosphere hydrogen. Hydrogen was then pumped off under dynamic vacuum for 45 minutes at the reduction temperature, the temperature was lowered to 40° C. and an 8 point isotherm (with pressures between 80 and 400 torr) was obtained. $H_2$ was used as the chemisorption probe molecule. The sample was evacuated at the chemisorption temperature to remove any weakly adsorbed hydrogen and the titration repeated to determine the weak adsorption isotherm. Subtraction of the two isotherms yields the strongly chemisorbed isotherm and its extrapolated intercept at 0 torr corresponds to monolayer gas coverage. This value was used to estimate nickel dispersions (based on a H/Ni surface ratio of 1).

The reductions are repeated at the same [450° C.] reduction temperature [for 90 minute intervals] to make certain that all the Ni that will reduce at the given temperature has actually reduced. These samples were then evacuated at the reduction temperature and the combined and weak hydrogen adsorption isotherms were measured at 40° C. Successive reduction cycles check that additional nickel was not being reduced. In Table 8, we indicate the chemisorption values for the Ni catalysts of Examples 37 and 40. The data show the dramatic increase in Ni dispersion when the Ni is deposited using the process of the present invention.

TABLE 8

| Samples (nominal compositions) | Treatment | Strong hydrogen chemisorption H/Ni in % |
| --- | --- | --- |
| 19.0% Ni/$SiO_2$ | Example 37, aqueous no addition | 3.9 |
| 18.3% Ni/$SiO_2$ | Example 40, triethanolamine addition | 13.7 |

Example 42

Evaluation of Sulfur Adsorption Capacities of the Materials of Examples 37 to 40

All four Ni-based samples of Examples 37 to 40 were evaluated for sulfur adsorption capacities in the following manner. 8 cc's of the adsorbent were charged to a stainless steel reaction tube (L/D of 18) which was placed in a flow-through reaction unit heated with a tube furnace. The adsorbent was then reduced in flowing $H_2$ (200 cc/min) at 350° C. by ramping at 2° C./min from room temperature to 350° C. and holding for 2 hrs. After holding at 350° C. for 2 hrs., the samples were cooled to 200° C. A gasoline-range hydrocarbon blend containing 80 ppm sulfur as thiophene was then introduced to the Ni-based adsorbent. The experiments were run under the following conditions: (210 psig, 200° C., 1 LHSV) in an up-flow mode. Sulfur capacities were calculated based on a measurement (ANTEK sulfur) of total sulfur remaining in the product. The results are provided in Table 9.

TABLE 9

| Samples (nominal compositions) | Treatments | Sulfur capacity % wt S |
| --- | --- | --- |
| 19.0% Ni/SiO2 | Example 37, aqueous | 0.16 |
| 18.0% Ni/$SiO_2$ | Example 38, triethanolamine added to solution molar ratio triethanolamine/Ni = 0.125 | 0.43 |
| 18.0% Ni/$SiO_2$ | Example 39, triethanolamine added to solution molar ratio triethanolamine/Ni = 0.25 | 0.56 |
| 18.3% Ni/$SiO_2$ | Example 40, triethanolamine added to solution molar ratio triethanolamine/Ni = 0.50 | 0.69 |

As can be seen from the data sulfur levels of less than 1 ppm were achieved for all samples. The sulfur capacity was greatest for the adsorbents of the present invention. Surprisingly, the sulfur capacities directly relate to the amount of triethanolamine dispersant used in adsorbent preparation and are all far superior to a sample prepared without any dispersant.

Example 43

Determination of the Decomposition Temperature for Various Organic Complexes

Figure 11:
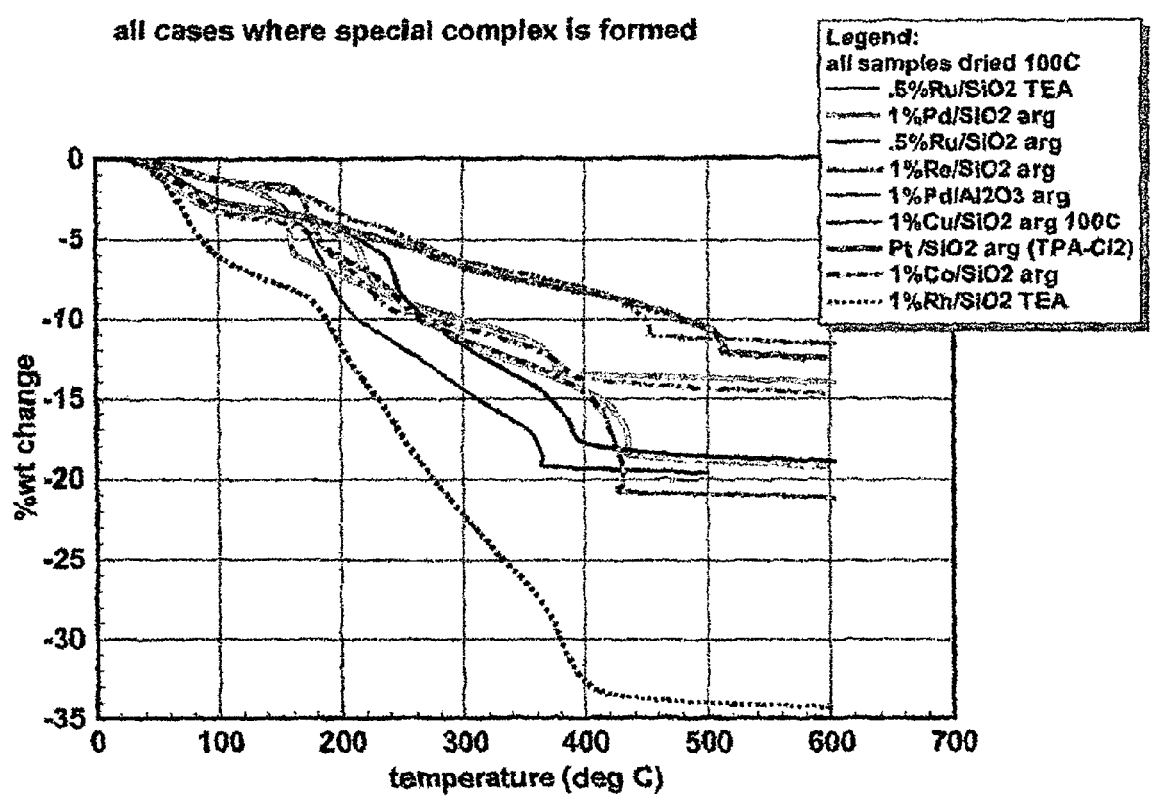
FIG. 11 shows the air treatment TGA plots for a variety of supported metal organic complexes (1 to 5 wt % metal/support), which have been dried at 100° C. after formation of the organic complex.

A number of supported organic complexes derived from various metals and nitrogen containing compounds and deposited on either silica of alumina were subjected to air treatment TGA and the decomposition profile for each determined. The TGA data is presented in FIG. 11 where TEA is triethanolamine, arg is L-arginine, and arg (TPA-Cl2) is arginine complex with tetramine Pt dichloride as Pt salt.

TABLE 1

| Sample of 0.5% Ru Supported on SiO$_2$ | Reduction temperature | % dispersion (combined) | % dispersion (weak) | % dispersion (strong) |
|---|---|---|---|---|
| Example 7 Ru-TEA/300° C. | 250 | 0 | 0 | 0.0 |
| | 325 | 0 | 0 | 0.0 |
| | 400 | 63.1 | 28.9 | 34.1 |
| | 400 | 66.4 | 29.7 | 36.7 |
| | 400 | 65.8 | 28.6 | 37.3 |
| | 400 | 65.8 | 29.0 | 36.9 |
| Example 8 Ru-TEA/400° C. | 250 | 16.18 | 7 | 9.2 |
| | 325 | 9.46 | 3.97 | 5.5 |
| | 400 | 8.69 | 1.67 | 7.0 |
| | 400 | 6.66 | 0 | 6.7 |

TABLE 2

| Sample of 0.5% Ru Supported on SiO$_2$ | Reduction temperature | % dispersion (combined) | % dispersion (weak) | % dispersion (strong) |
|---|---|---|---|---|
| Example 10 Ru/TEA/275° C. air | 250 | 0 | 0 | 0.0 |
| | 325 | 0 | 0 | 0.0 |
| | 400 | 57.6 | 29.9 | 27.7 |
| | 400 | 55.3 | 31.7 | 23.6 |
| Example 11 Ru/TEA/400° C. N$_2$ | 250 | 0 | 0 | 0.0 |
| | 325 | 0 | 0 | 0.0 |
| | 400 | 52.8 | 25.9 | 26.9 |
| | 400 | 60.8 | 30.6 | 30.2 |
| | 400 | 64.6 | 31.4 | 33.2 |
| | 400 | 64.7 | 31.5 | 33.2 |

TABLE 3

| Sample of 0.5% Ru Supported on SiO$_2$ | Reduction temperature | % dispersion (combined) | % dispersion (weak) | % dispersion (strong) |
|---|---|---|---|---|
| Example 7 Ru-TEA/300° C. | 250 | 0 | 0 | 0.0 |
| | 325 | 0 | 0 | 0.0 |
| | 400 | 63.1 | 28.9 | 34.1 |
| | 400 | 66.4 | 29.7 | 36.7 |
| | 400 | 65.8 | 28.6 | 37.3 |
| | 400 | 65.8 | 29.0 | 36.9 |
| Example 12 Ru-aq/100° C. | 150 | 77.77 | 40.87 | 36.9 |
| | 200 | 72.68 | 38.24 | 34.4 |
| | 250 | 66.54 | 36.51 | 30.0 |
| | 325 | 53.99 | 32.64 | 21.4 |
| | 400 | 45.98 | 27.67 | 18.3 |
| | 400 | 43.65 | 27.2 | 16.5 |
| | 400 | 42.64 | 25.84 | 16.8 |
| Example 13 Ru-aq/300° C. | 250 | 1.22 | 0 | 1.2 |
| | 325 | 0.38 | 0 | 0.4 |
| | 400 | 0.23 | 0 | 0.2 |

TABLE 4

| Sample of 0.5% Ru Supported on SiO$_2$ | Reduction temperature | % dispersion (combined) | % dispersion (weak) | % dispersion (strong) |
|---|---|---|---|---|
| Example 7 Ru-TEA/300° C. | 250 | 0 | 0 | 0.0 |
| | 325 | 0 | 0 | 0.0 |
| | 400 | 63.1 | 28.9 | 34.1 |
| | 400 | 66.4 | 29.7 | 36.7 |
| | 400 | 65.8 | 28.6 | 37.3 |
| | 400 | 65.8 | 29.0 | 36.9 |
| Example 14 Ru-arginine/250° C. | 250 | 0 | 0 | 0.0 |
| | 325 | 0 | 0 | 0.0 |
| | 400 | 65.09 | 33.4 | 31.7 |
| | 400 | 68.91 | 34.42 | 34.5 |

TABLE 5

| Sample of 0.5% Ru Supported on SiO$_2$ | Reduction temperature | % dispersion (combined) | % dispersion (weak) | % dispersion (strong) |
|---|---|---|---|---|
| Example 9 Ru/TEA/dry 100 C air | 250 | 0 | 0 | 0.0 |
| | 400 | 48.87 | 30.02 | 18.9 |
| | 400 | 49.79 | 29.3 | 20.5 |
| | 400 | 49.86 | 30.55 | 19.3 |
| Example 10 Ru/TEA/275° C. air | 250 | 0 | 0 | 0.0 |
| | 325 | 0 | 0 | 0.0 |
| | 400 | 57.6 | 29.9 | 27.7 |
| | 400 | 55.3 | 31.7 | 23.6 |

TABLE 6

| Samples (nominal compositions) | Treatments | Strong hydrogen chemisorption H/Co in % | TEM Particle size ($D_{sv}$) (nm) |
|---|---|---|---|
| 11% Co, 1% Re/3% ZrO$_2$/TiO$_2$ (anatase) | | | |
| Example 21 | no posttreat or addition | 4.9 | |
| Example 22 | N,N dimethylethanolamine posttreat dried impregnate | 8.6 | 5.1 |
| Example 23 | N,N dimethylethanolamine posttreat calcined oxide | 6.8 | |
| 11% Co, 0.15% Re/TiO$_2$ (rutile) | | | |
| Example 24 | N,N methyldiethanolamine posttreat dried impregnate | 3.9 | 7.5 |

TABLE 6-continued

| Samples (nominal compositions) | Treatments | Strong hydrogen chemisorption H/Co in % | TEM Particle size ($D_{sv}$) (nm) |
|---|---|---|---|
| 11% Co, 1% Re/TiO$_2$ (rutile) | | | |
| Example 28 11% Co, 0.15% Re/1% ZrO$_2$/TiO$_2$ (rutile) | no posttreat or addition | 4.0 | 10.2 |
| Example 26 10.6% Co, 0.7% Re/1% ZrO$_2$/TiO$_2$ (rutile) | Triethanolamine added to solution | 3.9 | 7.5 |
| Example 27 Co, Re/SiO$_2$ | no posttreat or addition | 3.6 | 13.7 |
| Example 29 | Triethanolamine added to solution | 11.5 | 5.9 |
| Example 30 | No posttreat or addition | 2.1 | |

The invention claimed is:

1. A process for the manufacture of a catalyst comprising a catalytically active metal dispersed on a support, which process comprises:
   a) preparing a support having an organic metal complex of the catalytically active metal deposited thereon by treating a porous support with a compound or salt of the metal and a nitrogen-containing organic compound selected from (i) amino acids and (ii) compounds containing both an amino group and an alcohol group, to form the organic metal complex on the support;
   b) partially decomposing the organic metal complex on the support to the extent that the partially decomposed product (I) retains between 10 and 95% by weight of the dry weight attributed to the organic metal complex prior to partial decomposition, and (II) exhibits one or more infra-red absorption bands between 2100-2200 cm$^{-1}$ that are not present in the organic metal complex before partial decomposition; and
   c) converting the partially decomposed organic metal complex into catalytically active metal.

2. The process as claimed in claim 1 wherein the conversion to catalytically active metal is achieved by treatment of the support comprising the partially decomposed organic metal complex with a reductant.

3. The process as claimed in claim 2 wherein the reductant is selected from a source of hydrogen, a source of CO, and mixtures thereof.

4. The process as claimed in claim 2 wherein the source of reductant is provided in-situ in a catalysed process.

5. The process as claimed in claim 2 wherein the source of reductant is provided in a catalyst regeneration process.

6. The process as claimed in claim 2 wherein the source of reductant is provided in a catalyst regeneration process or catalyst recycle process associated with a catalysed process.

7. The process as claimed in claim 1 wherein the nitrogen-containing organic compound has been incorporated into or within the support during its manufacture or synthesis.

8. The process as claimed in claim 1 wherein the nitrogen-containing organic compound is an aliphatic amine containing one or more hydroxyl groups.

9. The process as claimed in claim 8 wherein the amine comprises an hydroxyalkyl group.

10. The process as claimed in claim 9 wherein the hydroxyalkyl group is $C_1$-$C_{50}$-hydroxyalkyl.

11. The process as claimed in claim 10 wherein the hydroxyalkyl group is $C_1$-$C_8$-hydroxyalkyl.

12. The process as claimed in claim 11 wherein the hydroxyalkyl group is $C_1$-$C_4$-hydroxyalkyl.

13. The process as claimed in claim 12 wherein the hydroxyalkyl group is selected from: hydroxymethyl, 1-hydroxyethyl, 2-hydroxyethyl, 1-hydroxy-n-propyl, 2-hydroxy-n-propyl, 3-hydroxy-n-propyl and 1-hydroxy-methyl-ethyl.

14. The process as claimed in claim 13 wherein the nitrogen-containing organic compound comprises a mono-, di-, or tri-, substituted aliphatic hydroxyalkylamine.

15. The process as claimed in claim 14 wherein the hydroxyalkylamine comprises one or more of: methanolamine, di-methanolamine, tri-methanolamine, ethanolamine, di-ethanolamine, tri-ethanolamine, butanolamine, di-butanolamine, tri-butanolamine, propanolamine, di-propanolamine, dimethylethanolamine, di-isopropylethanolamine, methyldiethanolamine, dimethylamino-2-propanol and tri-propanolamine.

16. The process of claim 1 wherein the amino acid is L-arginine.

17. The process as claimed in claim 1 wherein the amino acid is selected from all isomers of the following: alanine, arginine, asparagines, aspartic acid, cysteine, cystine, 3,5-dibromotyrosine, 3,5-diiodotyrosine, glutamic acid, glutamine, glycine, histidine, hydroxylysine, hydroxyproline, isoleucine, leucine, lysine, methionine, phenylalanine, proline, serine, threonine, thyroxine, tryptophane, tyrosine and valine.

18. The process of claim 1, wherein the organic metal complex is partially decomposed by calcination or pyrolysis, wherein the calcination temperature is less than the temperature, as determined by TGA in air, at which total weight loss of the organic complex occurs or the pyrolysis temperature is less than the temperature, as determined by TGA in an inert atmosphere of hydrogen, at which total weight loss of the organic complex occurs.

19. The process as claimed in claim 18 wherein the calcination or pyrolysis temperature is between 200° C. and the temperature at which total weight loss of the organic complex occurs.

20. The process as claimed in claim 18 wherein the partial decomposition is performed by introduction of the support comprising the organic metal complex into a process selected from the group consisting of a catalysed process, a catalyst regeneration process, and a catalyst recycle process.

21. The process as claimed in claim 1 wherein, in the catalyst formed by the process, the total metal dispersion is 45% or more and the metal dispersion relating to a strongly chemisorbed component of the total metal dispersion is 20% or greater.

22. The process as claimed in claim 1 wherein the product of step (b) exhibits dispersion values relating to the strong dispersion component of less than 1%.

23. The process as claimed in claim 22 wherein the dispersion is less than 0.5%.

24. The process as claimed in claim 1 wherein step (b) is performed to the extent that the partially decomposed product retains between 20 and 75% by weight of the dry weight attributed to the organic complex prior to partial decomposition.

25. The process as claimed in claim 1 wherein the catalyst support comprises silica.

26. The process as claimed in claim 25 wherein the silica is amorphous.

27. The process as claimed in claim 1 wherein the support comprises a material selected from the group consisting of an ordered mesoporous material, a macroporous material, and a combination thereof.

28. The process as claimed in claim 1 wherein the support comprises a material designated as M41S.

29. The process as claimed in claim 28 wherein the support material is MCM-41.

30. The process as claimed in claim 1 wherein the support comprises alumina.

31. The process as claimed in claim 1 wherein the support comprises a material selected from the group consisting of rutile titanium dioxide, anatase titanium dioxide and mixtures thereof.

32. The process as claimed in claim 31 wherein the support further comprises zirconium dioxide.

33. The process as claimed in claim 1 wherein the salt or compound of one or more catalytically active metals is a salt or compound of one or more metals selected from the group consisting of: Group 1 (Group IA); Group 2 (Group IIA); Group 3 (Group IIIA, IIIB); Group 4 (Group IVA, IVB); Group 5 (Group VA, VB); Group 6 (Group VIA, VIB); Group 7 (Group VIIA, VIIB); Groups 8, 9, and 10 (Group VIII, VIIIA); Group 11 (Group IB); Group 12 (Group IIB), Group 13 (Group IIIA, IIIB); and Group 14 (Group IVA, IVB).

34. The process as claimed in claim 33 wherein the salt or compound of one or more catalytically active metals is a salt or compound of one or more metals selected from the group consisting of copper, platinum, rhodium, palladium, cobalt, iron, nickel, rhenium, ruthenium and mixtures of two or more thereof as active metal.

35. The process according to claim 1 wherein the compound or salt of the catalytically active metal is selected from a nitrate and nitrosyl nitrate.

36. A process for the production of $C_{5+}$ liquid hydrocarbons from a hydrogen and carbon monoxide synthesis gas by contact of the said gas at reaction conditions with a catalyst as manufactured by the process as claimed in claim 1.

37. A method for the removal of sulfur from a mixture comprising one or more organic compounds and one or more sulfur containing compounds, in which method the mixture is contacted with one or more materials comprising active metal dispersed on an inorganic support under such conditions that sulfur is adsorbed onto the material comprising active metal dispersed on an inorganic support and wherein the material comprising active metal deposited on a support is a catalyst as manufactured by the process as claimed in claim 1.

\* \* \* \* \*